(12) United States Patent
Nothacker et al.

(10) Patent No.: US 12,343,133 B1
(45) Date of Patent: Jul. 1, 2025

(54) METHOD AND SYSTEM FOR DETECTING AND MAINTAINING PERFORMANCE OF AN ALCOHOL SENSING DEVICE

(71) Applicant: KHN Solutions, LLC, San Francisco, CA (US)

(72) Inventors: Keith Harry Nothacker, San Francisco, CA (US); Raymond Kampmeier, San Francisco, CA (US); William Tammen, San Francsico, CA (US); Imraan Aziz, San Francisco, CA (US)

(73) Assignee: KHN Solutions, LLC, San Francisco, CA (US)

( * ) Notice: Subject to any disclaimer, the term of this patent is extended or adjusted under 35 U.S.C. 154(b) by 0 days.

(21) Appl. No.: 18/922,156

(22) Filed: Oct. 21, 2024

Related U.S. Application Data

(60) Provisional application No. 63/593,858, filed on Oct. 27, 2023.

(51) Int. Cl.
  *A61B 5/08* (2006.01)
  *A61B 5/00* (2006.01)
  *A61B 5/145* (2006.01)

(52) U.S. Cl.
  CPC .......... *A61B 5/082* (2013.01); *A61B 5/14517* (2013.01); *A61B 5/4845* (2013.01);
  (Continued)

(58) Field of Classification Search
  CPC ....... G01N 33/4972; G01N 2001/2244; G01N 33/497; A61B 5/14546; A61B 5/681; A61B 5/0002; A61B 5/082; A61B 5/097; A61B 5/6898; B60W 2540/24; Y10S 436/90; Y10T 436/204165
  (Continued)

(56) References Cited

U.S. PATENT DOCUMENTS

| 3,824,538 A | 7/1974 | Slemp |
| 4,487,055 A | 12/1984 | Wolf |

(Continued)

FOREIGN PATENT DOCUMENTS

| CN | 104781820 | 7/2015 |
| DE | 4327312 | 1/2015 |

(Continued)

OTHER PUBLICATIONS

"STIC Search Results. 15205876-528781—Search Results.pdf, Sep. 18, 2003.", Oct. 11, 2017 00:00:00.0.

(Continued)

*Primary Examiner* — John E Breene
*Assistant Examiner* — Truong D Phan
(74) *Attorney, Agent, or Firm* — Jeffrey Schox; Ivan Wong

(57) ABSTRACT

The technologies described enable tracking statuses of and performance metrics for alcohol sensing devices, with respect to performing device integrity checks in order to ensure that testing of provided samples is performed properly. Systems described include alcohol testing devices including flow tubes, alcohol sensors, pumps, supplementary sensors, processors, and user interfaces. Methods described include steps for performing a set of integrity checks in coordination with receiving samples (e.g., breath samples, transdermal samples, etc.) from users.

18 Claims, 18 Drawing Sheets

(52) U.S. Cl.
CPC ............ *A61B 5/681* (2013.01); *A61B 5/6898* (2013.01); *A61B 2560/0228* (2013.01); *A61B 2560/0252* (2013.01); *A61B 2560/0276* (2013.01)

(58) Field of Classification Search
USPC .................................................. 73/23.3, 23.2
See application file for complete search history.

(56) References Cited

U.S. PATENT DOCUMENTS

| | | | |
|---|---|---|---|
| 4,738,333 A | 4/1988 | Collier et al. | |
| 4,749,553 A | 6/1988 | Lopez et al. | |
| 4,902,628 A | 2/1990 | Blair | |
| 4,914,038 A | 4/1990 | Jewitt | |
| 4,996,161 A | 2/1991 | Conners et al. | |
| 5,157,601 A | 10/1992 | Jones et al. | |
| D333,441 S | 2/1993 | Greene | |
| 5,216,415 A | 6/1993 | Ono et al. | |
| 5,220,919 A | 6/1993 | Phillips et al. | |
| 5,248,617 A * | 9/1993 | De Haan ................. F23N 5/003 422/90 | |
| 5,291,898 A | 3/1994 | Wolf | |
| 5,416,468 A | 5/1995 | Baumann | |
| 5,422,485 A | 6/1995 | Bowlds | |
| 5,426,415 A | 6/1995 | Prachar et al. | |
| 5,433,863 A | 7/1995 | Braden et al. | |
| D362,642 S | 9/1995 | Howse | |
| D381,885 S | 8/1997 | Lane | |
| 5,944,661 A | 8/1999 | Swette et al. | |
| 6,026,674 A | 2/2000 | Gammenthaler | |
| 6,075,444 A | 6/2000 | Sohege et al. | |
| 6,433,863 B1 | 8/2002 | Weiss | |
| 6,454,723 B1 | 9/2002 | Montagnino | |
| 6,556,905 B1 | 4/2003 | Mittelsteadt et al. | |
| 6,608,399 B2 | 8/2003 | McConnell et al. | |
| 6,726,636 B2 | 4/2004 | Der et al. | |
| 6,748,792 B1 | 6/2004 | Freund et al. | |
| 6,824,520 B2 | 11/2004 | Orr et al. | |
| 6,853,956 B2 | 2/2005 | Ballard et al. | |
| 6,858,182 B1 | 2/2005 | Ito et al. | |
| 6,899,683 B2 | 5/2005 | Mault et al. | |
| 6,956,484 B2 | 10/2005 | Crespo | |
| 6,958,691 B1 | 10/2005 | Anderson et al. | |
| D521,885 S | 5/2006 | Eddy et al. | |
| D530,424 S | 10/2006 | Manser et al. | |
| D539,683 S | 4/2007 | Shaw et al. | |
| D539,684 S | 4/2007 | Kitamura et al. | |
| 7,204,335 B2 | 4/2007 | Stewart et al. | |
| 7,256,700 B1 | 8/2007 | Ruocco et al. | |
| 7,311,665 B2 | 12/2007 | Hawthorne et al. | |
| 7,341,693 B2 | 3/2008 | Der et al. | |
| 7,451,852 B2 | 11/2008 | Stewart et al. | |
| 7,462,149 B2 | 12/2008 | Hawthorne et al. | |
| D586,677 S | 2/2009 | Nothacker et al. | |
| D603,281 S | 11/2009 | Gonzalez | |
| 7,611,461 B2 | 11/2009 | Hawthorne et al. | |
| 7,611,611 B2 | 11/2009 | Belt | |
| D606,434 S | 12/2009 | Castrodale et al. | |
| 7,636,047 B1 | 12/2009 | Sempek | |
| 7,641,611 B2 | 1/2010 | Hawthorne et al. | |
| 7,823,681 B2 | 11/2010 | Crespo et al. | |
| 7,930,927 B2 | 4/2011 | Cooper et al. | |
| 7,934,577 B2 | 5/2011 | Walter et al. | |
| 8,040,233 B2 | 10/2011 | Adappa et al. | |
| 8,078,334 B2 | 12/2011 | Goodrich | |
| 8,126,735 B2 | 2/2012 | Dicks et al. | |
| 8,165,824 B2 | 4/2012 | Iiams et al. | |
| 8,240,419 B2 | 8/2012 | Zimmermann et al. | |
| 8,258,968 B2 | 9/2012 | Ghazarian et al. | |
| 8,280,436 B2 | 10/2012 | Harris | |
| 8,317,697 B2 | 11/2012 | Hawthorne et al. | |
| 8,359,901 B2 | 1/2013 | Freund et al. | |
| 8,370,027 B2 | 2/2013 | Pettersson et al. | |
| 8,381,573 B2 | 2/2013 | Keays | |
| 8,453,492 B2 | 6/2013 | Tsuzuki et al. | |
| 8,466,796 B1 | 6/2013 | Mejia et al. | |
| 8,505,360 B2 | 8/2013 | Ruocco et al. | |
| 8,525,668 B1 | 9/2013 | Alouani et al. | |
| 8,549,318 B2 | 10/2013 | White et al. | |
| 8,560,010 B2 | 10/2013 | Koehn | |
| 8,590,364 B2 | 11/2013 | Lopez et al. | |
| 8,657,744 B2 | 2/2014 | Rompa et al. | |
| 8,693,597 B2 | 4/2014 | Sexton et al. | |
| 8,707,758 B2 | 4/2014 | Keays | |
| D705,100 S | 5/2014 | Nothacker et al. | |
| 8,808,228 B2 | 8/2014 | Brister et al. | |
| 8,814,804 B2 | 8/2014 | Walden et al. | |
| 8,844,337 B2 | 9/2014 | Kountotsis et al. | |
| 8,849,387 B2 | 9/2014 | Gilbert et al. | |
| 8,862,152 B1 | 10/2014 | Buchholz et al. | |
| 8,878,669 B2 | 11/2014 | Nothacker et al. | |
| 8,899,748 B1 | 12/2014 | Migdal | |
| 8,920,725 B2 | 12/2014 | Withrow et al. | |
| 8,941,501 B1 | 1/2015 | Debijl | |
| 8,957,771 B2 | 2/2015 | Arringdale et al. | |
| D724,980 S | 3/2015 | Nothacker et al. | |
| D727,763 S | 4/2015 | Nothacker et al. | |
| D727,764 S | 4/2015 | Nothacker et al. | |
| 9,011,657 B2 | 4/2015 | Parselle et al. | |
| 9,020,773 B2 | 4/2015 | Son et al. | |
| D731,341 S | 6/2015 | Kobayakawa | |
| 9,045,101 B2 | 6/2015 | Phelan | |
| 9,063,120 B2 | 6/2015 | Park | |
| 9,076,317 B2 | 7/2015 | Nothacker et al. | |
| 9,095,251 B2 | 8/2015 | Purks et al. | |
| 9,192,324 B2 | 11/2015 | Phillips et al. | |
| 9,192,334 B2 | 11/2015 | Nothacker et al. | |
| 9,228,997 B2 | 1/2016 | Keays | |
| 9,239,323 B2 | 1/2016 | Keays | |
| 9,241,054 B1 | 1/2016 | Roberts | |
| 9,241,659 B2 | 1/2016 | Rompa et al. | |
| 9,241,661 B2 | 1/2016 | Shnaper et al. | |
| 9,250,228 B2 | 2/2016 | Nothacker et al. | |
| 9,278,696 B2 | 3/2016 | Yi et al. | |
| 9,301,719 B2 | 4/2016 | Abreu | |
| 9,316,614 B2 | 4/2016 | Stock et al. | |
| 9,355,579 B2 | 5/2016 | Buck et al. | |
| 9,398,858 B2 | 7/2016 | Phillips et al. | |
| 9,417,232 B2 | 8/2016 | Keays et al. | |
| 9,442,103 B1 | 9/2016 | Goad | |
| 9,481,245 B2 | 11/2016 | Nelson | |
| 9,489,487 B2 | 11/2016 | Hawthorne et al. | |
| 9,609,921 B1 | 4/2017 | Feinstein | |
| 9,643,186 B1 | 5/2017 | Ahmad et al. | |
| 9,662,065 B2 | 5/2017 | Nothacker et al. | |
| 9,664,638 B2 | 5/2017 | Chu et al. | |
| 9,707,845 B1 | 7/2017 | Nienhouse | |
| 9,746,456 B2 | 8/2017 | Keays | |
| 9,781,984 B2 | 10/2017 | Baranski et al. | |
| 9,788,772 B2 | 10/2017 | Nothacker et al. | |
| 9,820,114 B2 | 11/2017 | Greenhut et al. | |
| 9,829,480 B2 | 11/2017 | Wojcik et al. | |
| 9,848,815 B2 | 12/2017 | Abreu | |
| 9,855,000 B2 | 1/2018 | Lansdorp et al. | |
| 9,867,539 B2 | 1/2018 | Heikenfeld et al. | |
| 9,872,649 B2 | 1/2018 | Nothacker et al. | |
| 9,881,997 B2 | 1/2018 | Sakata et al. | |
| 9,915,644 B2 | 3/2018 | Nothacker et al. | |
| 9,922,508 B2 | 3/2018 | Keays et al. | |
| 10,040,349 B2 | 8/2018 | Devries et al. | |
| 10,154,460 B1 * | 12/2018 | Miller .................... A61B 5/742 |
| 10,182,752 B2 | 1/2019 | Nothacker et al. | |
| 10,352,923 B2 | 7/2019 | Nothacker et al. | |
| 10,631,767 B2 | 4/2020 | Nothacker et al. | |
| 10,987,038 B2 | 4/2021 | Nothacker et al. | |
| 11,006,895 B2 | 5/2021 | Nothacker et al. | |
| 11,278,222 B2 | 3/2022 | Moeller et al. | |
| 11,324,449 B2 | 5/2022 | Nothacker et al. | |
| 11,471,079 B2 | 10/2022 | Nothacker et al. | |
| 11,602,306 B2 | 3/2023 | Nothacker | |
| 11,646,120 B2 | 5/2023 | Nothacker et al. | |
| 11,666,703 B2 | 6/2023 | Newberry et al. | |
| 11,674,949 B2 | 6/2023 | Moeller | |

(56) References Cited

U.S. PATENT DOCUMENTS

| | | |
|---|---|---|
| 11,701,007 B2 | 7/2023 | Hanson et al. |
| 2002/0008966 A1 | 1/2002 | Fjelstad et al. |
| 2002/0084130 A1 | 7/2002 | Der et al. |
| 2002/0089660 A1 | 7/2002 | Weiss |
| 2002/0128769 A1 | 9/2002 | Der et al. |
| 2002/0140289 A1 | 10/2002 | McConnell et al. |
| 2002/0143267 A1 | 10/2002 | Montagnino |
| 2003/0028120 A1 | 2/2003 | Mault et al. |
| 2003/0116159 A1 | 6/2003 | Orr et al. |
| 2003/0117287 A1 | 6/2003 | Crespo |
| 2003/0146841 A1 | 8/2003 | Koenig |
| 2003/0176803 A1 | 9/2003 | Gollar |
| 2003/0177119 A1 | 9/2003 | Cole |
| 2003/0208110 A1 | 11/2003 | Mault et al. |
| 2004/0233058 A1 | 11/2004 | Dodds |
| 2004/0233061 A1 | 11/2004 | Johns |
| 2004/0236199 A1 | 11/2004 | Hawthorne et al. |
| 2004/0242976 A1 | 12/2004 | Abreu |
| 2005/0053523 A1 | 3/2005 | Brooke |
| 2005/0124694 A1 | 6/2005 | Vanmoor |
| 2005/0184870 A1 | 8/2005 | Galperin et al. |
| 2005/0241871 A1 | 11/2005 | Stewart et al. |
| 2006/0182661 A1 | 8/2006 | Aquila |
| 2006/0193749 A1 | 8/2006 | Ghazarian et al. |
| 2006/0217624 A1 | 9/2006 | Myklebust et al. |
| 2006/0217625 A1 | 9/2006 | Forrester |
| 2006/0237252 A1 | 10/2006 | Mobley et al. |
| 2006/0237253 A1 | 10/2006 | Mobley et al. |
| 2006/0282344 A1 | 12/2006 | Brown |
| 2006/0293613 A1 | 12/2006 | Fatehi et al. |
| 2007/0024454 A1 | 2/2007 | Singhal |
| 2007/0093725 A1 | 4/2007 | Shaw |
| 2007/0107728 A1 | 5/2007 | Ricciardelli et al. |
| 2007/0144812 A1 | 6/2007 | Stewart et al. |
| 2007/0296601 A1 | 12/2007 | Sultan et al. |
| 2008/0045806 A1 | 2/2008 | Keppler |
| 2008/0097793 A1 | 4/2008 | Dicks et al. |
| 2008/0169924 A1 | 7/2008 | Belden |
| 2008/0183388 A1 | 7/2008 | Goodrich |
| 2008/0216561 A1 | 9/2008 | Cooper et al. |
| 2008/0262469 A1 | 10/2008 | Brister et al. |
| 2009/0043409 A1 | 2/2009 | Ota |
| 2009/0090577 A1 | 4/2009 | Takahashi et al. |
| 2009/0111486 A1 | 4/2009 | Burstrom |
| 2009/0164141 A1 | 6/2009 | Lee |
| 2009/0182216 A1 | 7/2009 | Roushey et al. |
| 2009/0187111 A1 | 7/2009 | Reilly et al. |
| 2009/0201138 A1 | 8/2009 | Ghazarian et al. |
| 2009/0212957 A1 | 8/2009 | Burris |
| 2009/0309711 A1 | 12/2009 | Adappa et al. |
| 2010/0010689 A1 | 1/2010 | Yasushi et al. |
| 2010/0012417 A1 | 1/2010 | Walter et al. |
| 2010/0036592 A1 | 2/2010 | Osaki et al. |
| 2010/0108425 A1 | 5/2010 | Crespo et al. |
| 2010/0121502 A1 | 5/2010 | Katayama et al. |
| 2010/0152976 A1 | 6/2010 | White et al. |
| 2010/0234064 A1 | 9/2010 | Harris |
| 2010/0268425 A1 | 10/2010 | Pettersson et al. |
| 2010/0274411 A1 | 10/2010 | Ozaki |
| 2010/0294583 A1 | 11/2010 | Biondo et al. |
| 2010/0310011 A1 | 12/2010 | Sexton et al. |
| 2011/0079073 A1 | 4/2011 | Keays |
| 2011/0266160 A1 | 11/2011 | Campbell et al. |
| 2011/0291827 A1 | 12/2011 | Baldocchi et al. |
| 2011/0304465 A1 | 12/2011 | Boult et al. |
| 2011/0308297 A1 | 12/2011 | Tsuzuki et al. |
| 2011/0309932 A1 | 12/2011 | Arringdale et al. |
| 2012/0020837 A1 | 1/2012 | Withrow et al. |
| 2012/0031165 A1 | 2/2012 | Ruocco et al. |
| 2012/0075094 A1 | 3/2012 | Keays |
| 2012/0130261 A1 | 5/2012 | Fujita et al. |
| 2012/0132524 A1 | 5/2012 | Parselle et al. |
| 2012/0157871 A1 | 6/2012 | Walden et al. |
| 2012/0172679 A1 | 7/2012 | Logan et al. |
| 2012/0330175 A1 | 12/2012 | Phillips et al. |
| 2013/0021153 A1 | 1/2013 | Keays |
| 2013/0035602 A1 | 2/2013 | Gemer |
| 2013/0111979 A1 | 5/2013 | Park |
| 2013/0123570 A1 | 5/2013 | Ly et al. |
| 2013/0150727 A1 | 6/2013 | Phillips et al. |
| 2013/0218039 A1 | 8/2013 | Sotos et al. |
| 2013/0253360 A1 | 9/2013 | Wang et al. |
| 2013/0281873 A1 | 10/2013 | Evans et al. |
| 2013/0282321 A1 | 10/2013 | Son et al. |
| 2013/0305808 A1 | 11/2013 | Yoo |
| 2014/0003676 A1 | 1/2014 | Baughman et al. |
| 2014/0012143 A1 | 1/2014 | Gilbert et al. |
| 2014/0032596 A1 | 1/2014 | Fish et al. |
| 2014/0052567 A1 | 2/2014 | Bhardwaj et al. |
| 2014/0059066 A1 | 2/2014 | Koloskov |
| 2014/0062703 A1 | 3/2014 | Purks et al. |
| 2014/0062722 A1 | 3/2014 | Ofir et al. |
| 2014/0086590 A1 | 3/2014 | Ganick et al. |
| 2014/0135612 A1 | 5/2014 | Yuen et al. |
| 2014/0165697 A1 | 6/2014 | Mochizuki et al. |
| 2014/0165698 A1 | 6/2014 | Mochizuki et al. |
| 2014/0188398 A1 | 7/2014 | Cohen et al. |
| 2014/0204334 A1 | 7/2014 | Stoll |
| 2014/0210627 A1 | 7/2014 | Nothacker et al. |
| 2014/0234172 A1 | 8/2014 | Burgi et al. |
| 2014/0240132 A1 | 8/2014 | Bychkov |
| 2014/0247343 A1 | 9/2014 | Chen |
| 2014/0273858 A1 | 9/2014 | Panther et al. |
| 2014/0281523 A1 | 9/2014 | Golino |
| 2014/0303836 A1 | 10/2014 | Phelan |
| 2014/0311215 A1 | 10/2014 | Keays et al. |
| 2014/0361900 A1 | 12/2014 | Nothacker et al. |
| 2014/0365142 A1 | 12/2014 | Baldwin |
| 2014/0371603 A1 | 12/2014 | Fujita et al. |
| 2015/0084774 A1 | 3/2015 | Wojcik et al. |
| 2015/0164416 A1 | 6/2015 | Nothacker et al. |
| 2015/0251660 A1 | 9/2015 | Nelson |
| 2015/0325104 A1 | 11/2015 | Greenhut et al. |
| 2015/0359469 A1 | 12/2015 | Jacobs et al. |
| 2015/0360696 A1 | 12/2015 | Yi et al. |
| 2016/0001781 A1 | 1/2016 | Fung et al. |
| 2016/0021228 A1 | 1/2016 | Roberts |
| 2016/0284200 A1 | 9/2016 | Song et al. |
| 2016/0318521 A1 | 11/2016 | Nothacker et al. |
| 2016/0324442 A1 | 11/2016 | Zdeblick |
| 2016/0338627 A1 | 11/2016 | Lansdorp et al. |
| 2016/0349239 A1 | 12/2016 | Chien |
| 2017/0014035 A1 | 1/2017 | Newberry |
| 2017/0079574 A1 | 3/2017 | Rodriguez Restrepo et al. |
| 2017/0086714 A1 | 3/2017 | Nothacker et al. |
| 2017/0086743 A1 | 3/2017 | Bushnell et al. |
| 2017/0103166 A1 | 4/2017 | Oh et al. |
| 2017/0231571 A1 | 8/2017 | Rogers et al. |
| 2017/0303819 A1* | 10/2017 | Nothacker ............ G08B 21/18 |
| 2017/0313189 A1 | 11/2017 | Walter et al. |
| 2017/0354354 A1 | 12/2017 | Nothacker et al. |
| 2018/0049668 A1 | 2/2018 | Defant et al. |
| 2018/0074029 A1 | 3/2018 | Devries et al. |
| 2018/0074030 A1 | 3/2018 | Devries et al. |
| 2018/0085058 A1 | 3/2018 | Chakravarthi et al. |
| 2018/0086264 A1 | 3/2018 | Pedersen |
| 2018/0101721 A1 | 4/2018 | Nienhouse |
| 2018/0164285 A1 | 6/2018 | Nothacker et al. |
| 2018/0184920 A1 | 7/2018 | Rabinovich et al. |
| 2018/0209955 A1 | 7/2018 | Moeller |
| 2018/0263538 A1 | 9/2018 | Heikenfeld et al. |
| 2018/0347493 A1* | 12/2018 | Tascillo ................ F02D 41/22 |
| 2019/0246958 A1 | 8/2019 | Moeller et al. |
| 2019/0290197 A1 | 9/2019 | Nothacker et al. |
| 2020/0101982 A1 | 4/2020 | Bowers et al. |
| 2020/0124589 A1 | 4/2020 | Gonzales |
| 2020/0372824 A1 | 11/2020 | Hanson et al. |
| 2021/0100493 A1 | 4/2021 | Ben Oren et al. |
| 2021/0128060 A1* | 5/2021 | Sarcinelli ............ A61B 5/0022 |
| 2022/0039478 A1* | 2/2022 | Lavanchy ............ G06K 7/1413 |
| 2022/0061680 A1 | 3/2022 | Hanson et al. |
| 2022/0192597 A1 | 6/2022 | Feldman |
| 2022/0240849 A1 | 8/2022 | Spector et al. |
| 2023/0138641 A1 | 5/2023 | Graham et al. |

(56) References Cited

U.S. PATENT DOCUMENTS

| | | |
|---|---|---|
| 2023/0190188 A1 | 6/2023 | Nothacker et al. |
| 2024/0008812 A1 | 1/2024 | Benson et al. |
| 2024/0306937 A1 | 9/2024 | Keays et al. |
| 2024/0310358 A1 | 9/2024 | Keays et al. |

FOREIGN PATENT DOCUMENTS

| | | | |
|---|---|---|---|
| FR | 2975522 A1 | 11/2012 | |
| KR | 100673261 B1 | 1/2007 | |
| KR | 20110038453 A * | 12/2011 | |
| WO | 2006066274 A2 | 6/2006 | |
| WO | WO-2017165709 A1 * | 9/2017 | ............. A61B 5/082 |

OTHER PUBLICATIONS

Kim, J., et al., "Noninvasive alcohol monitoring using a wearable tattoo-based iontophoretic-biosensing system", ACS Sensors. Jul. 12, 2016. vol. 1. No. 8; abstract.

Kuswandi, B., et al., "A simple visual ethanol biosensor based on alcohol oxidase immobilized onto polyaniline film for halal verification of fermented beverage samples", Sensors. 2014. vol. 14. No. 2; p. 2144, figure 6.

Nothacker, Keith Harry, et al., "Method and System for Detecting and Maintaining Performance of an Alcohol Sensing Device", U.S. Appl. No. 18/922,156, filed Oct. 21, 2024.

Zettl, Robert J., "The Determination of Blood Alcohol Concentration by Transdermal Measurement", Commissioned by Alcohol Monitoring Systems, Inc., Highlands Ranch, Colorado, Jul. 2002, 13 pages.

* cited by examiner

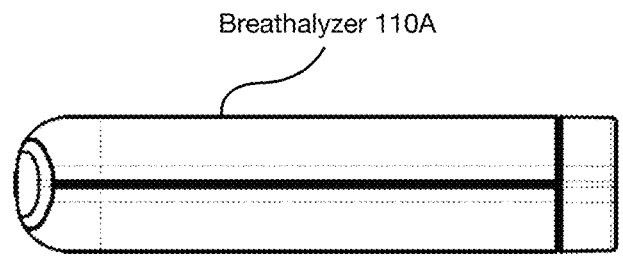
FIGURE 3E
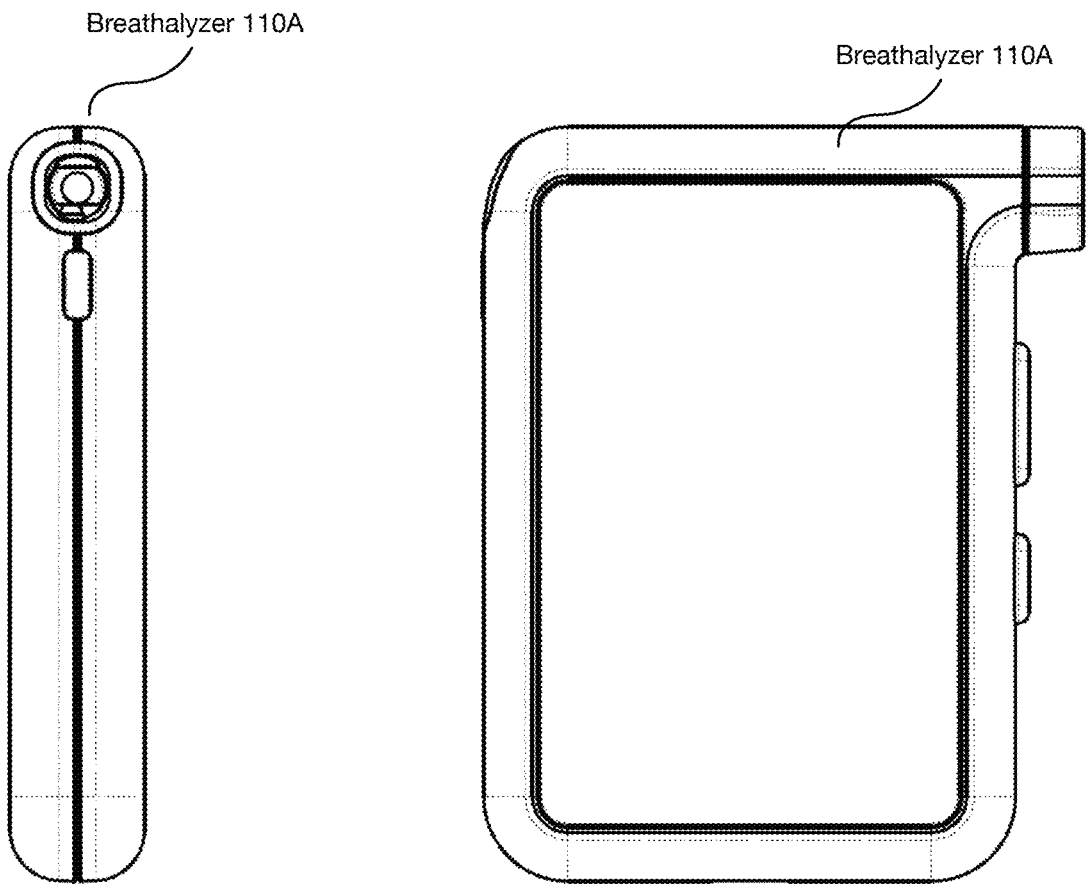
FIGURE 3F
FIGURE 3G

METHOD AND SYSTEM FOR DETECTING AND MAINTAINING PERFORMANCE OF AN ALCOHOL SENSING DEVICE

CROSS-REFERENCE TO RELATED APPLICATIONS

This application claims the benefit of U.S. Provisional Application Ser. No. 63/593,858 filed on 27 Oct. 2023, which is herein incorporated in its entirety by this reference.

TECHNICAL FIELD

This invention relates generally to the intoxication monitoring field, and more specifically to a new and useful system and method for detecting and maintaining performance of an alcohol sensing device in the intoxication monitoring field.

BACKGROUND

Alcohol sensing devices have expanded in usefulness, spanning a variety of use cases from commercial use to drunk driving prevention to criminal justice monitoring. These various use cases can all have different requirements for the confidence level of their measurements. Since these measurements can be affected by the health and age of the alcohol sensor(s), it is a significant limitation of conventional devices that they do not dynamically account for these contributing factors. Relatedly, existing alcohol sensing devices are further limited in relation to the following aspects: determination of alcohol sensing device integrity in coordination with user testing, improvement of user experience aspects, device tampering prevention, fraudulent alcohol sample provision, and other aspects.

Thus, there is a need in the intoxication monitoring field to create an improved and useful system and method for detecting and maintaining performance of an alcohol sensing device.

BRIEF DESCRIPTION OF THE FIGURES

FIG. 3E is a plan view of the top of a sample receiving device.

FIG. 3F is an elevation view of the back of a sample receiving device.

FIG. 3G is an elevation view of the right of a sample receiving device.

DESCRIPTION OF THE PREFERRED EMBODIMENTS

The following description of the preferred embodiments of the invention is not intended to limit the invention to these preferred embodiments, but rather to enable any person skilled in the art to make and use this invention.

1. Overview

Figure 1A:
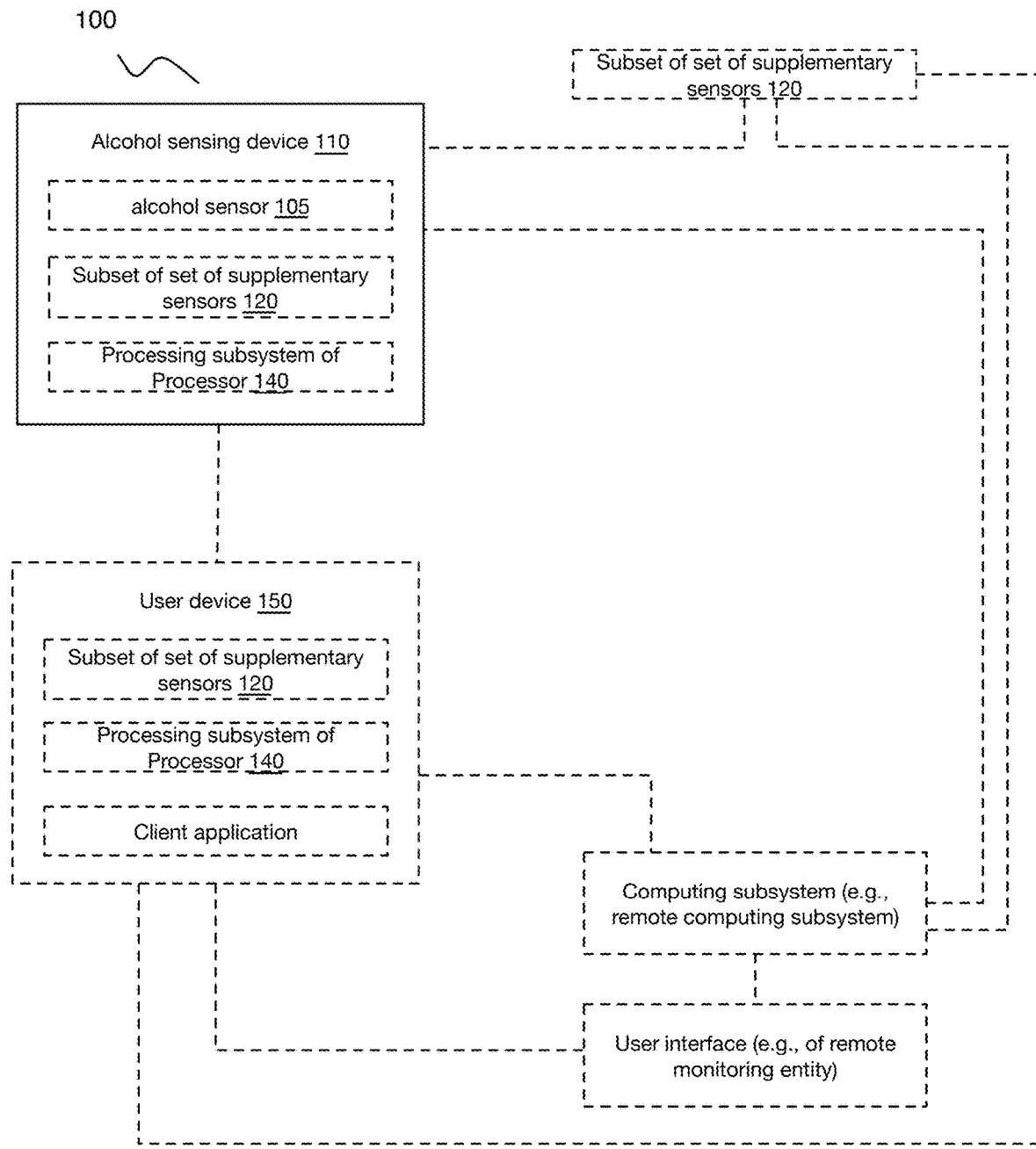
FIG. 1A is a schematic of an embodiment of a system for detecting and maintaining performance of an alcohol sensing device.

As shown in FIG. 1A, an embodiment of a system 100 for detecting and maintaining performance of an alcohol sensing device 110 includes a set of supplementary sensors 120.

Figure 1B:
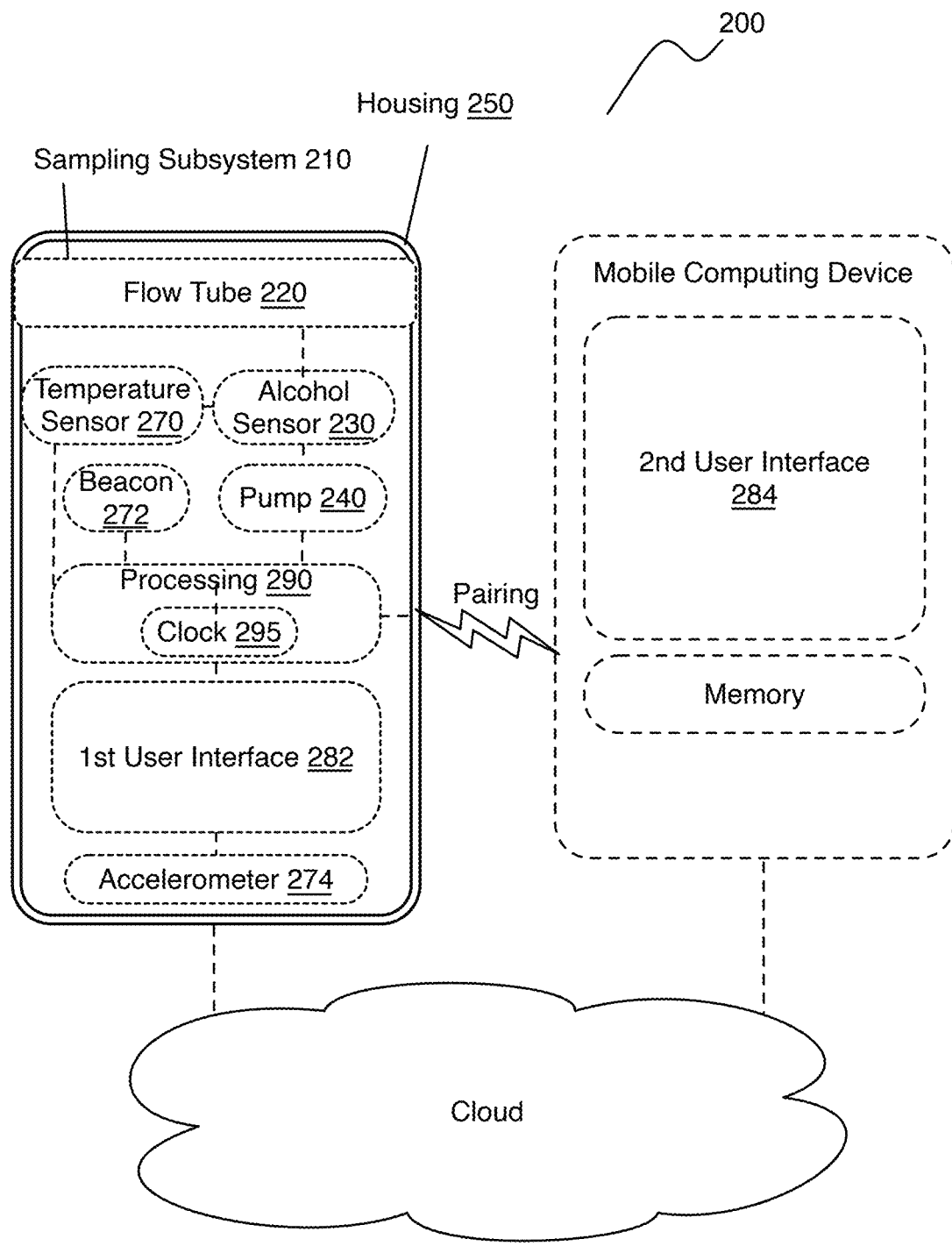
FIG. 1B is a schematic of an embodiment of a system for detecting and maintaining performance of an alcohol sensing device.

As shown in FIG. 1B, an embodiment of a system 200 for monitoring intoxication of a user includes: a sampling subsystem 210 comprising a flow tube 220, an alcohol sensor 230 in communication with the flow tube 220, and a pump 240 (e.g., solenoid pump) configured to deliver breath samples from the user through the flow tube 220 and to the alcohol sensor 230; a housing 250 surrounding the sampling subsystem 210; a mouthpiece 260 coupled to the flow tube 220 of the sampling subsystem 210; a temperature sensor 270 retained within the housing 250; a first user interface 282; and a processing subsystem 290 at least partially disposed within the housing 250 and comprising a clock 295, wherein the processing subsystem comprises instructions stored in non-transitory media that, when executed, perform one or more of the following steps: performing a first system integrity check with steps for determining proper function of the pump, performing a second system integrity check with steps for determining connectivity above a threshold level of connectivity with a mobile application interface, performing a third system integrity check with steps for calibrating the alcohol sensing device, performing a fourth system integrity check with steps for establishing communications with a cloud computing platform, and prompting the user to provide a breath sample to the alcohol sensing device upon satisfaction of the first system integrity check, the second system integrity check, the third system integrity check, and the fourth system integrity check. Aspects of system configurations and methods performed using embodiments of the systems 100, 200 and/or other system components are further described in detail below.

In variations, the processing subsystem 290 can further be configured for one or more of: receiving a temperature dataset from the temperature sensor, comparing a temperature metric to a threshold condition upon processing the temperature dataset, determining a time duration from a time point of testing of a previous breath sample received at the sampling subsystem, and transmitting instructions for prompting the user to provide a breath sample according to a testing protocol, wherein the testing protocol is modified based upon the temperature metric and the time duration. Aspects of system configurations and methods performed using embodiments of the systems 100, 200 and/or other system components are further described in detail below.

Additionally or alternatively, the system can include and/or interface with any or all of: the alcohol sensing device, a set of processors, and/or any other components. Further additionally or alternatively, the system can include and/or interface with any or all of the components as described in U.S. application Ser. No. 14/169,029, filed 30 Jan. 2014; U.S. application Ser. No. 14/602,919, filed 22 Jan. 2015; U.S. application Ser. No. 14/631,125, filed 25 Feb. 2015; U.S. application Ser. No. 15/375,801, filed 12 Dec. 2016; U.S. application Ser. No. 15/492,216, filed 20 Apr. 2017; U.S. application Ser. No. 16/362,444, filed 22 Mar. 2019; and U.S. application Ser. No. 17/033,501, filed 25 Sep. 2020; U.S. application Ser. No. 17/574,278, filed 12 Jan. 2022; and U.S. application Ser. No. 18/109,720, filed 14 Feb. 2023; each of which is incorporated herein in its entirety by this reference.

Figure 2A:
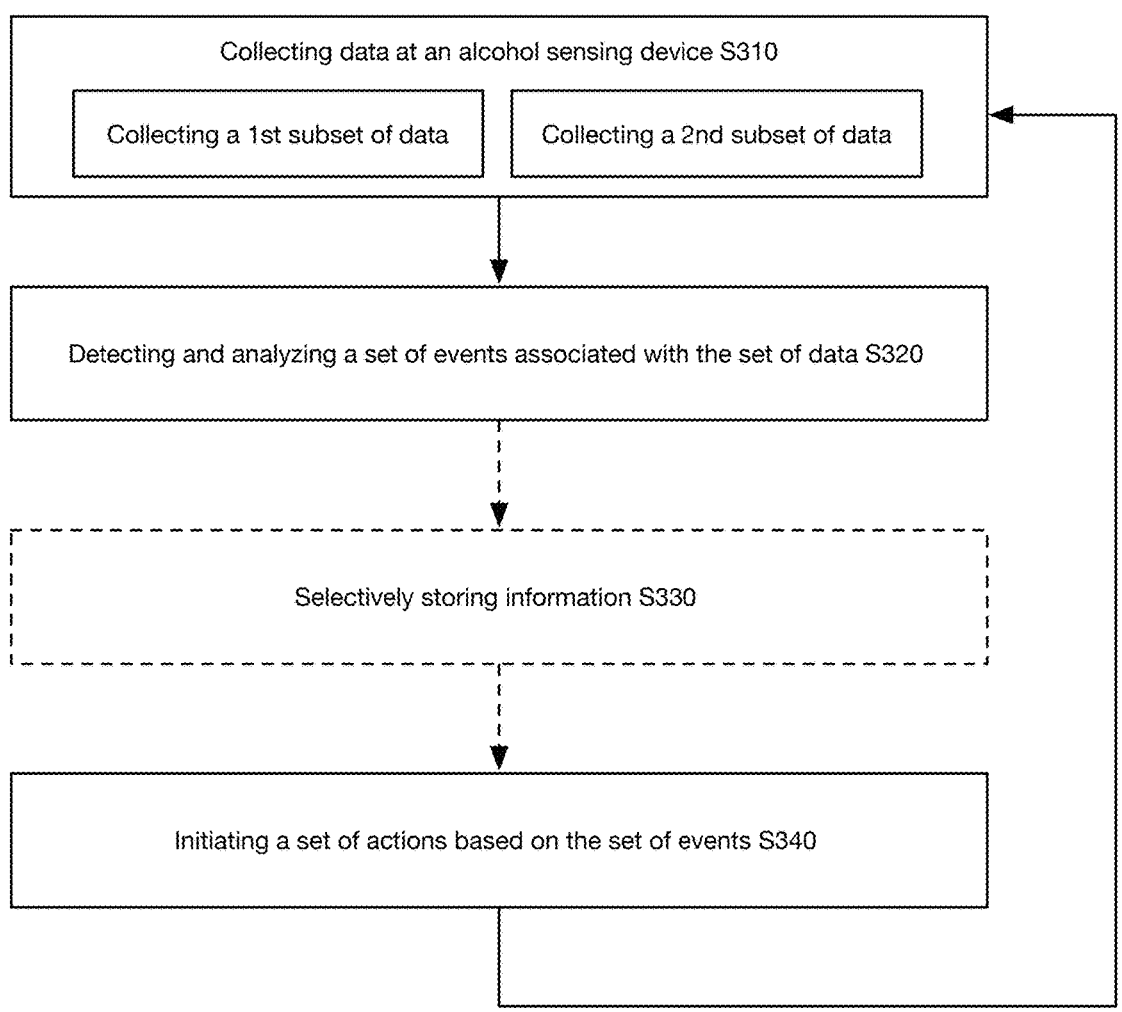
FIG. 2A is a schematic of an embodiment of a method for detecting and maintaining performance of an alcohol sensing device.

As shown in FIG. 2A, a method 300 for detecting and maintaining performance of an alcohol sensing device includes collecting data at an alcohol sensing device S310; detecting and analyzing a set of events associated with the set of data S320; and initiating a set of actions based on the set of events S340.

Figure 2B:
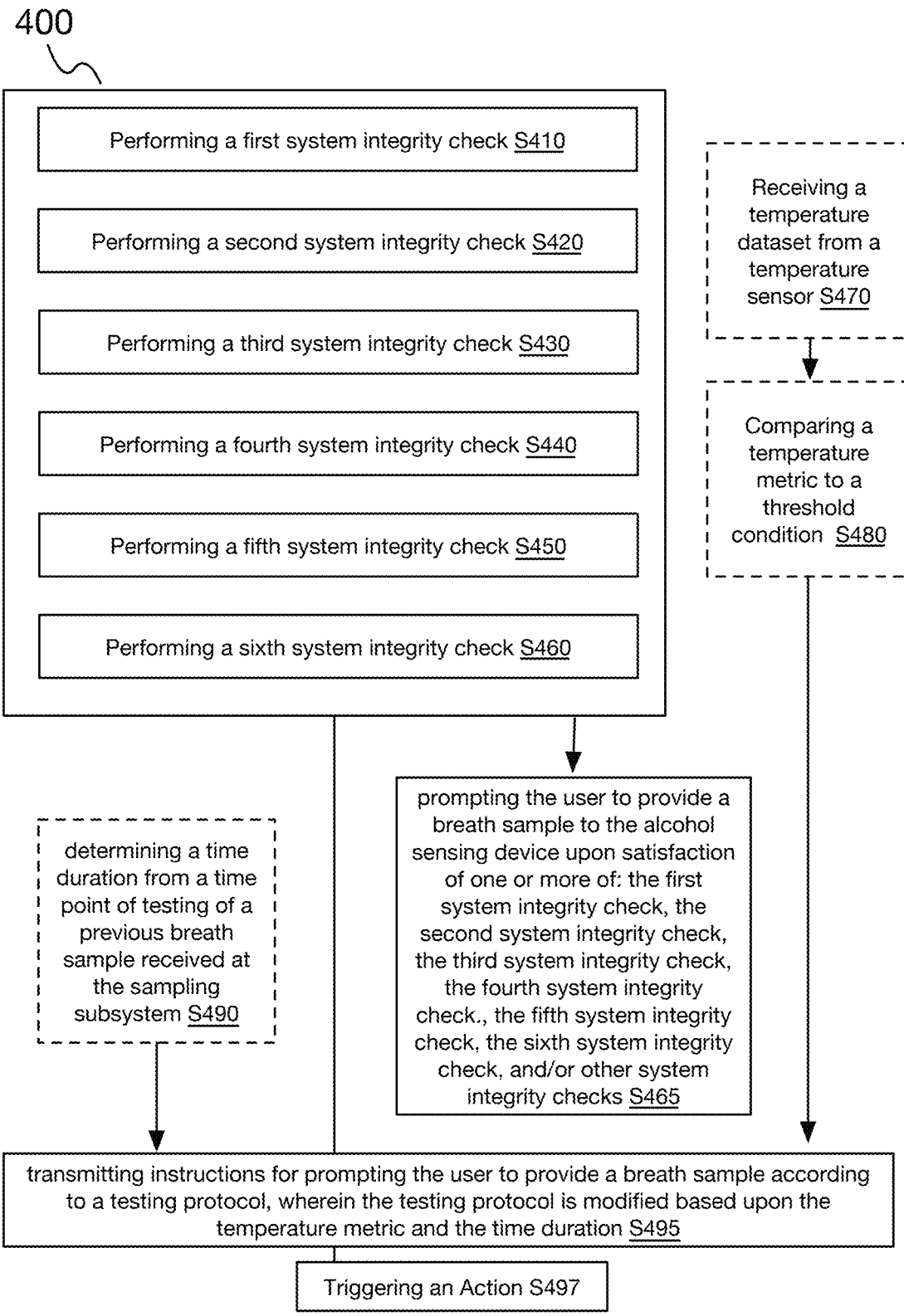
FIG. 2B is a schematic of an embodiment of a method for detecting and maintaining performance of an alcohol sensing device.
Figure 3A:
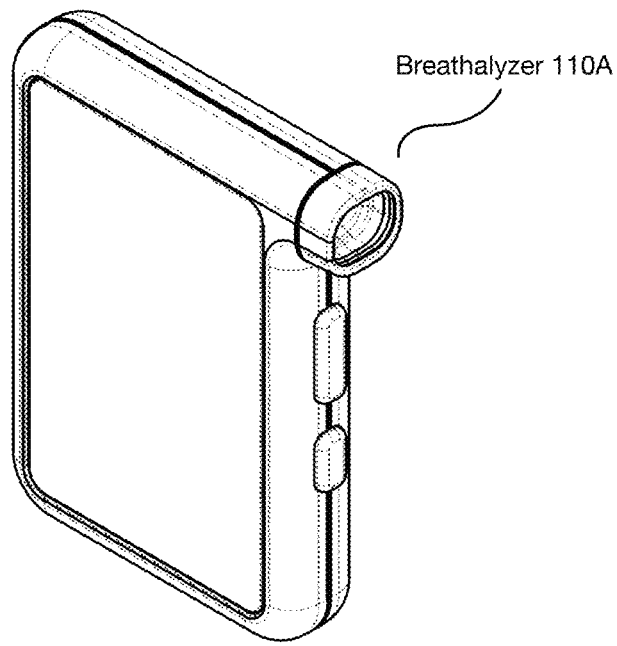
FIG. 3A is an isometric view from the front, top, left of a sample receiving device.
Figure 3B:
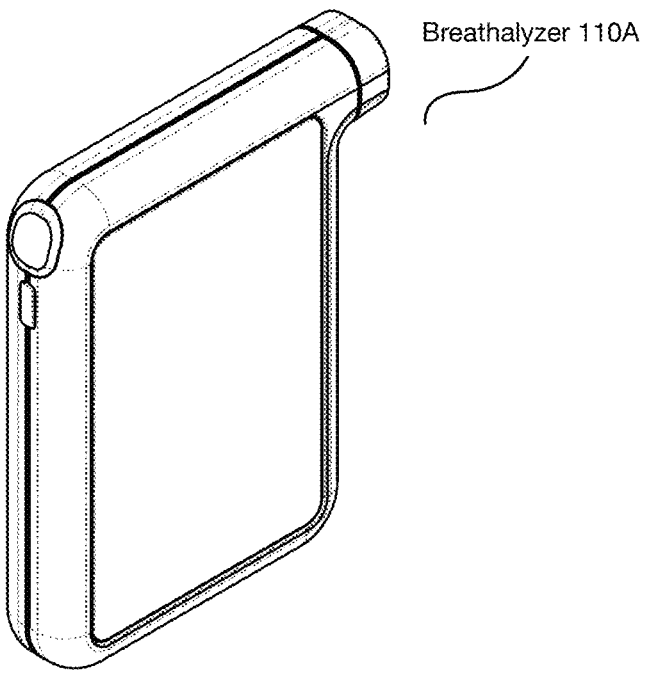
FIG. 3B is an isometric view from the back, top, right of a sample receiving device.
Figure 3C:
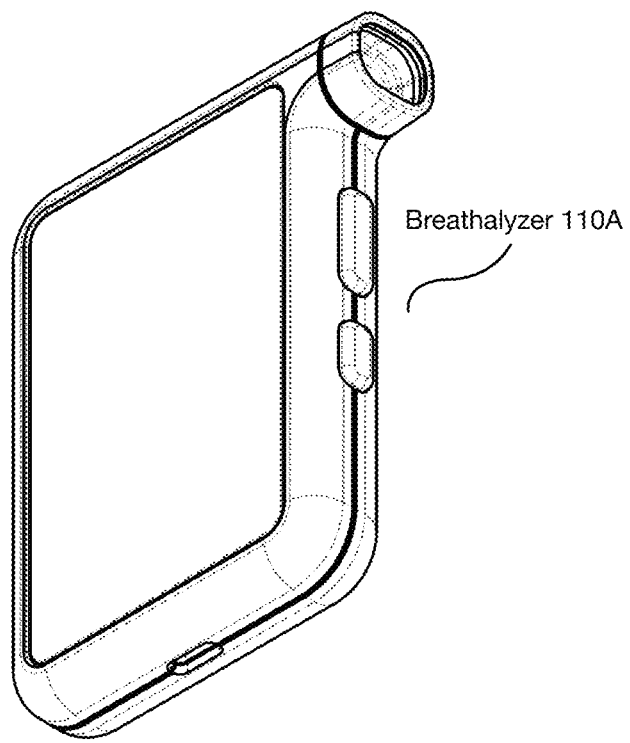
FIG. 3C is an isometric view from the front, bottom, left of a sample receiving device.
Figure 3D:
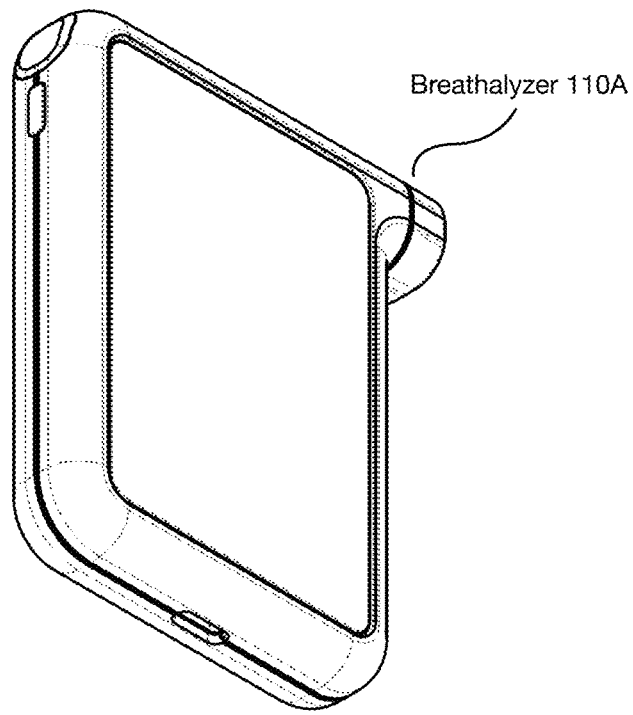
FIG. 3D is an isometric view from the back, bottom, right of a sample receiving device.
Figure 3H:
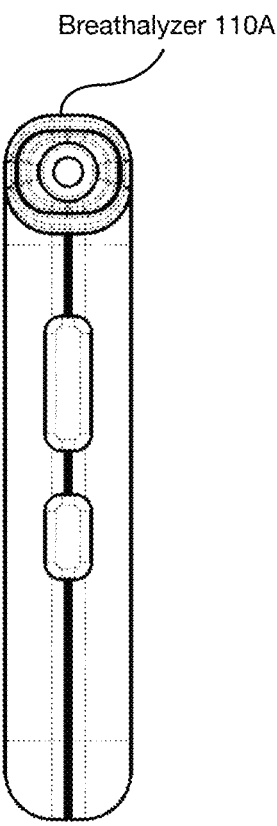
FIG. 3H is an elevation view of the front of a sample receiving device.
Figure 3I:
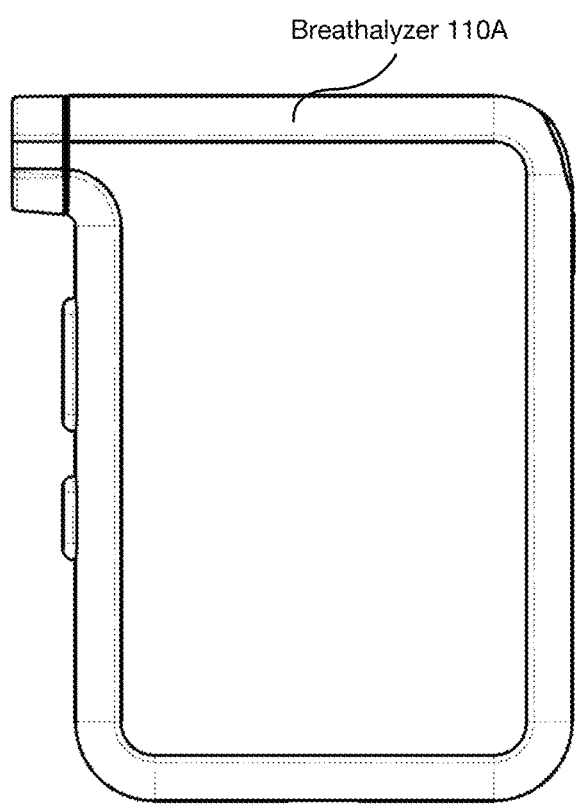
FIG. 3I is an elevation view of the left of a sample receiving device.
Figure 3J:
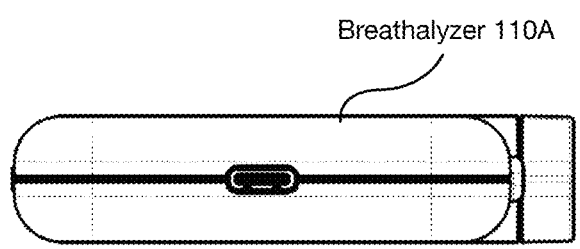
FIG. 3J is a plan view of the bottom of a sample receiving device.
Figure 4A:
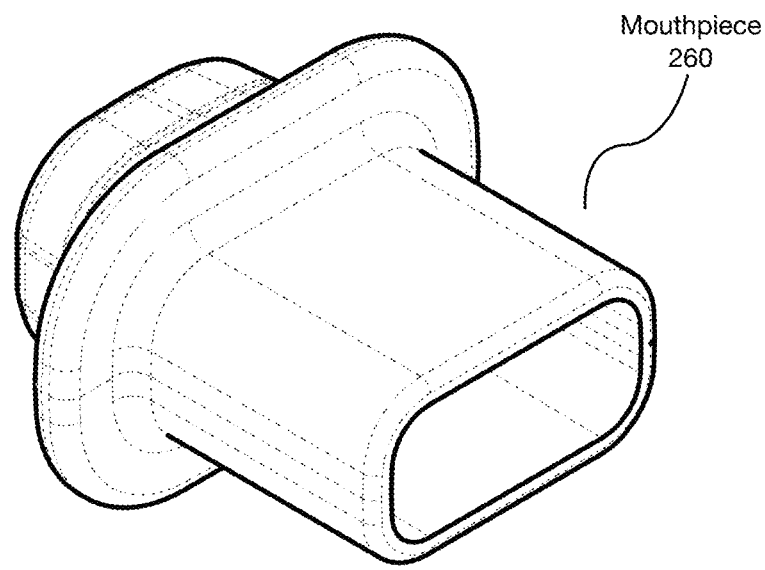
FIG. 4A is an isometric view from the front, top, left of a breathalyzer mouthpiece.
Figure 4B:
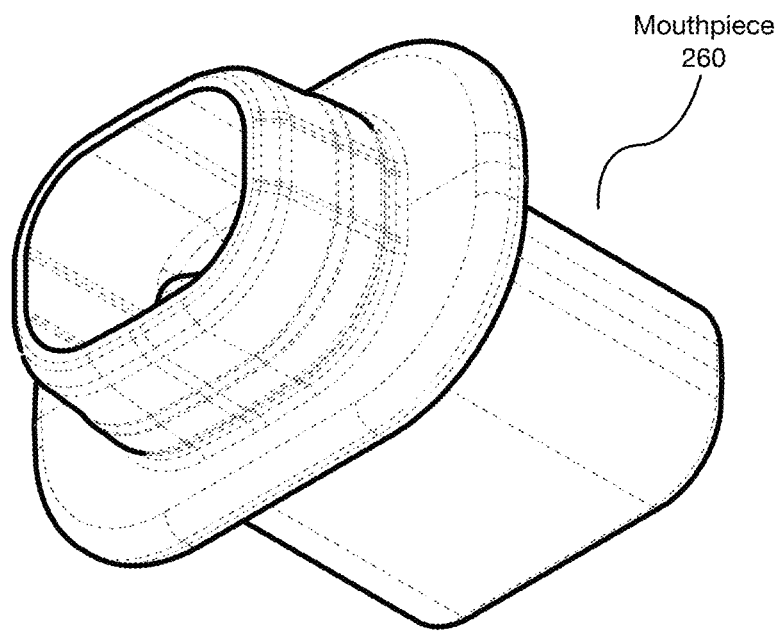
FIG. 4B is an isometric view from the back, bottom, right of a breathalyzer mouthpiece.
Figure 4C:
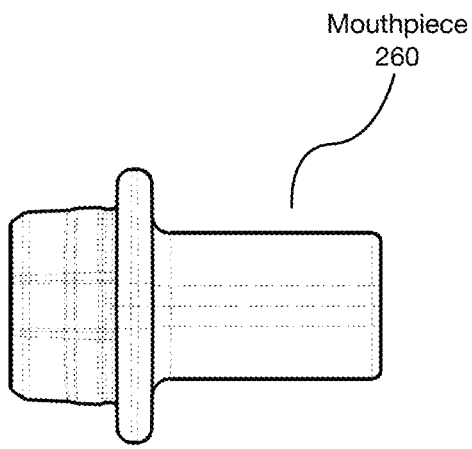
FIG. 4C is an elevation view of the right of a breathalyzer mouthpiece.
Figure 4D:
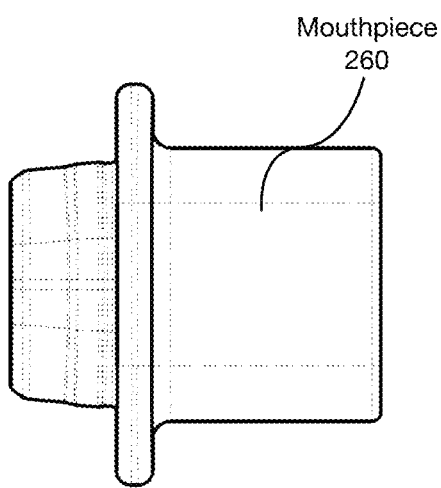
FIG. 4D is a plan view of the top of a breathalyzer mouthpiece.
Figure 4E:
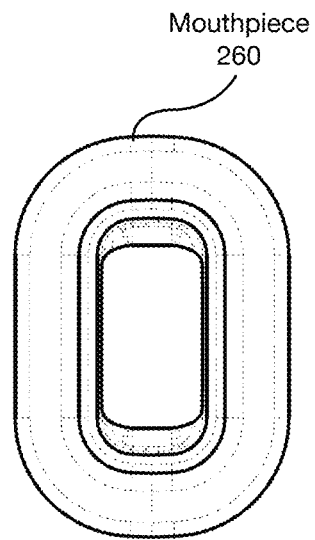
FIG. 4E is an elevation view of the front of a breathalyzer mouthpiece.
Figure 4F:
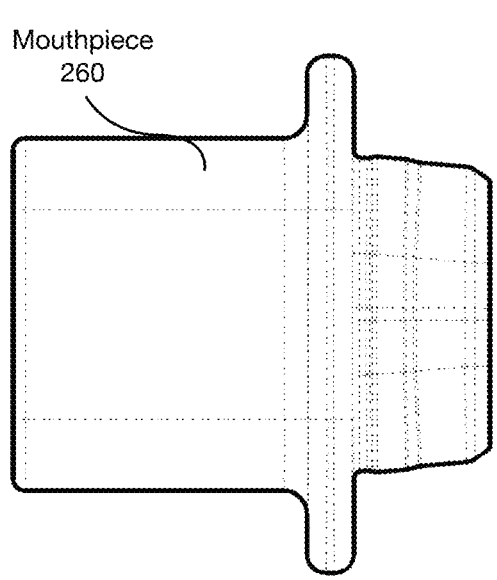
FIG. 4F is a plan view of the bottom of a breathalyzer mouthpiece.
Figure 4G:
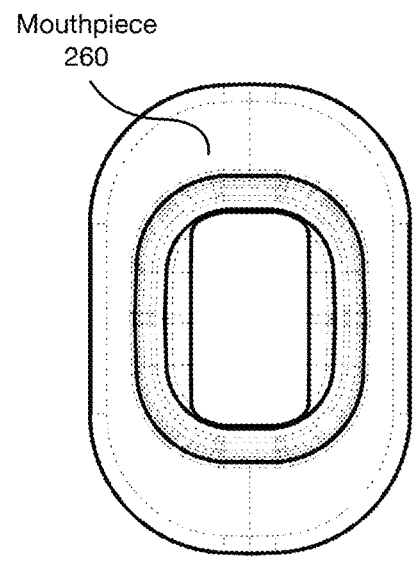
FIG. 4G is an elevation view of the back of a breathalyzer mouthpiece.
Figure 4H:
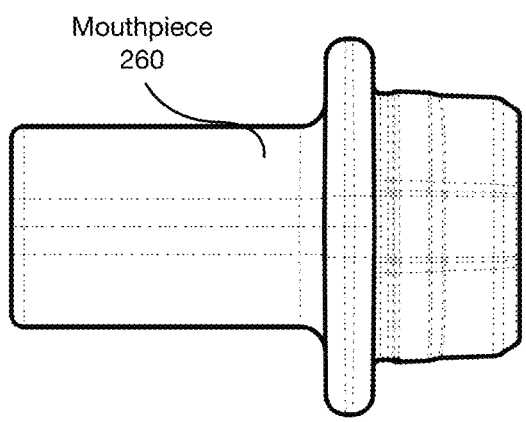
FIG. 4H is an elevation view of the left of a breathalyzer mouthpiece.

As shown in FIG. 2B, variations of the method 300 can include steps of method 400, which recites: for an alcohol sensing device comprising a flow tube, an alcohol sensor in communication with the flow tube, and a pump (e.g., solenoid pump) configured to deliver breath samples from the user through the flow tube and to the alcohol sensor: where the method 400 includes: performing a first system integrity check with steps for evaluating a set of conditions of an alcohol sensor of an alcohol sensing device S410; performing a second system integrity check with steps for evaluating a set of calibration data generated for the alcohol sensor S420; performing a third system integrity check with steps for evaluating environmental exposure conditions of the alcohol sensing device S430; performing a fourth system integrity check with steps for determining proper function of a pump of the alcohol sensing device S440; performing a fifth system integrity check with steps for evaluating malfunctioning of a processing subsystem and/or the alcohol sensor of the alcohol sensing device S450; and performing a sixth system integrity check with steps for evaluating a deviation between an actual alcohol sensor signal morphology and an expected alcohol sensor signal morphology (e.g., under ambient conditions) of the alcohol sensing device S460.

In some embodiments, the method 400 can further include one or more steps including: receiving a temperature dataset from the temperature sensor S470; comparing a temperature metric to a threshold condition upon processing the temperature dataset S480; determining a time duration from a time point of testing of a previous breath sample received at the sampling subsystem S490; and transmitting instructions for prompting the user to provide a breath sample according to a testing protocol, wherein the testing protocol is modified based upon the temperature metric and the time duration S495.

Additionally or alternatively, the methods 300, 400 can include any or all of: selectively storing information S330, any or all of the processes described in U.S. application Ser. No. 14/169,029, filed 30 Jan. 2014; U.S. application Ser. No. 14/602,919, filed 22 Jan. 2015; U.S. application Ser. No. 14/631,125, filed 25 Feb. 2015; U.S. application Ser. No. 15/375,801, filed 12 Dec. 2016; U.S. application Ser. No. 15/492,216, filed 20 Apr. 2017; U.S. application Ser. No. 16/362,444, filed 22 Mar. 2019; and U.S. application Ser. No. 17/033,501, filed 25 Sep. 2020; U.S. application Ser. No. 17/574,278, filed 12 Jan. 2022; and U.S. application Ser. No. 18/109,720, filed 14 Feb. 2023; each of which is incorporated in its entirety by this reference, or any other suitable processes performed in any suitable order. The method 200 can be performed with a system as described above and/or any other suitable system.

2. Benefits

The systems and methods for detecting and maintaining performance of an alcohol sensing device can confer several benefits over current systems and methods.

Embodiments of the technologies described confer the benefit of monitoring performance of alcohol sensing devices in an unprecedented manner, with respect to performing device integrity checks in order to ensure that testing of provided samples is performed properly. This provides significant benefits to the fields of alcohol testing, where reliance upon accuracy of tests is vital.

Embodiments of the technologies described confer the benefit of improving testing protocols in the field of alcohol sensing devices, where processing data that characterizes device and/or sample temperatures can improve the ways in which users are prompted to provide breath samples. For instance, processing data that characterizes device and/or sample temperatures can enhance user testing by guiding pre-heating of and/or pre-cooling of the alcohol sensing device and/or provided sample in coordination with testing.

Embodiments of the technologies described confer the benefit of improving testing protocols in the field of alcohol sensing devices, where processing data that characterizes timepoints and/or other aspects of prior tests can improve the ways in which users are prompted to provide breath samples. For instance, processing data that characterizes timepoints and/or other aspects of prior tests can enable method steps for initiating sample testing without requiring unnecessary sensor clearing time steps, thereby improving the speed at which samples are received and processed.

In variations, the inventions described can achieve sample testing within a duration of 1 minute, within a duration of 50 seconds, within a duration of 40 seconds, within a duration of 30 seconds, within a duration of 20 seconds, within a duration of 10 seconds, within a duration of 5 seconds, or less.

Embodiments of sample testing can entail test initiation (e.g., with opening of an application of a user interface that guides sample testing) through receiving testing results (e.g., with values of metrics that characterize the sample).

Embodiments of the technologies described confer the benefit of improving accuracy of sample testing, by dynamically guiding a user to provide samples according to different testing regimes (e.g., a timed breath sample testing regime, a volumetric testing regime, a deep lung sample testing regime, etc.) and/or transitioning between different testing regimes if a test result from one of a set of testing regimes does not satisfy a quality threshold condition (e.g., accuracy threshold condition, user authentication threshold condition, testing condition threshold condition, etc.).

Embodiments of the technologies described confer the benefit of improving enrollment in alcohol sample testing programs (e.g., by way of beacon devices integrated into such sample testing devices).

Embodiments of the technologies described confer the benefit of ensuring that only compatible device components are used, in order to ensure suitability of testing data resultant from provision of a sample. As an example, a removable mouthpiece of the alcohol sensing device can include a first communication component (e.g., near-field communication element) that is detectable by the alcohol sensing device and/or another device that is in communication with the alcohol sensing device. Signals detected from the first communication component can be used to verify that the removable mouthpiece element is a certified mouthpiece that is compatible with the alcohol sensing device.

Embodiments of the technologies described confer the benefit of providing improved operation modes, given that the alcohol sensing device can operate in an "awake" mode as long as a battery or other power source of the alcohol sensing device has a threshold level of energy.

Embodiments of the technologies described confer the benefit of supporting calibration of alcohol sensing devices in an unprecedented manner, as well as monitoring the health of a set of sensors more accurately and continuously, which can be used for any or all of: providing users or monitoring entities with feedback on the health of their alcohol sensing device(s); making adjustments to measurements derived from alcohol sensing data (e.g., to correct for known sensor impairment events), thereby increasing the accuracy of the measurement values; increasing an ease and/or efficiency with which a user replaces and/or recalibrates his or her device; and/or conferring any other benefit(s).

Embodiments of the technologies described confer the benefit of enabling or directly initiating actions commensurate with insights from monitoring sensors of the alcohol sensing device. In some examples, for instance, the system and/or method can function to increase a lifespan of the alcohol sensing device and/or prevent unnecessary replacements and calibrations by providing actionable insights related to how the user may be degrading his or her device, how the user can prevent and/or reverse this degradation, when the device needs to be replaced and/or recalibrated, and/or any other information.

Embodiments of the technologies described provide evidential-grade devices (e.g., evidential breath testing devices, etc.) that satisfy requirement of Department of Transportation (DOT) specifications for approval.

Additionally or alternatively, the system and method can confer any other benefit(s).

3. System

As shown in FIG. 1A, a system 100 for detecting and maintaining performance of an alcohol sensing device 110 includes a set of supplementary sensors 120. Additionally or alternatively, the system can include and/or interface with any or all of: the alcohol sensing device 110, a set of processors 140, and/or any other components. Further additionally or alternatively, the system can include and/or interface with any or all of the components as described in U.S. application Ser. No. 14/169,029, filed 30 Jan. 2014; U.S. application Ser. No. 14/602,919, filed 22 Jan. 2015; U.S. application Ser. No. 14/631,125, filed 25 Feb. 2015; U.S. application Ser. No. 15/375,801, filed 12 Dec. 2016; U.S. application Ser. No. 15/492,216, filed 20 Apr. 2017; U.S. application Ser. No. 16/362,444, filed 22 Mar. 2019; and U.S. application Ser. No. 17/033,501, filed 25 Sep. 2020; U.S. application Ser. No. 17/574,278, filed 12 Jan. 2022; and U.S. application Ser. No. 18/109,720, filed 14 Feb. 2023; each of which is incorporated in its entirety by this reference.

The system 100 preferably functions to collect data with which to assess an accuracy of alcohol measurements produced with an alcohol sensing device. Additionally, the system 100 can function to optimizing a timing of sensor replacement, assess a degree of sensor degradation, and/or perform any other functions.

The system 100 preferably includes and/or interfaces with an alcohol sensing device 110, such as any or all of those described in the applications described above that have been incorporated in their entirety by this reference. In a first set of variants, the alcohol sensing device 110 includes a breathalyzer 110A (e.g., as shown in FIGS. 3A-3J), which includes a removable mouthpiece shown in FIGS. 4A-4H.

Figure 5A:
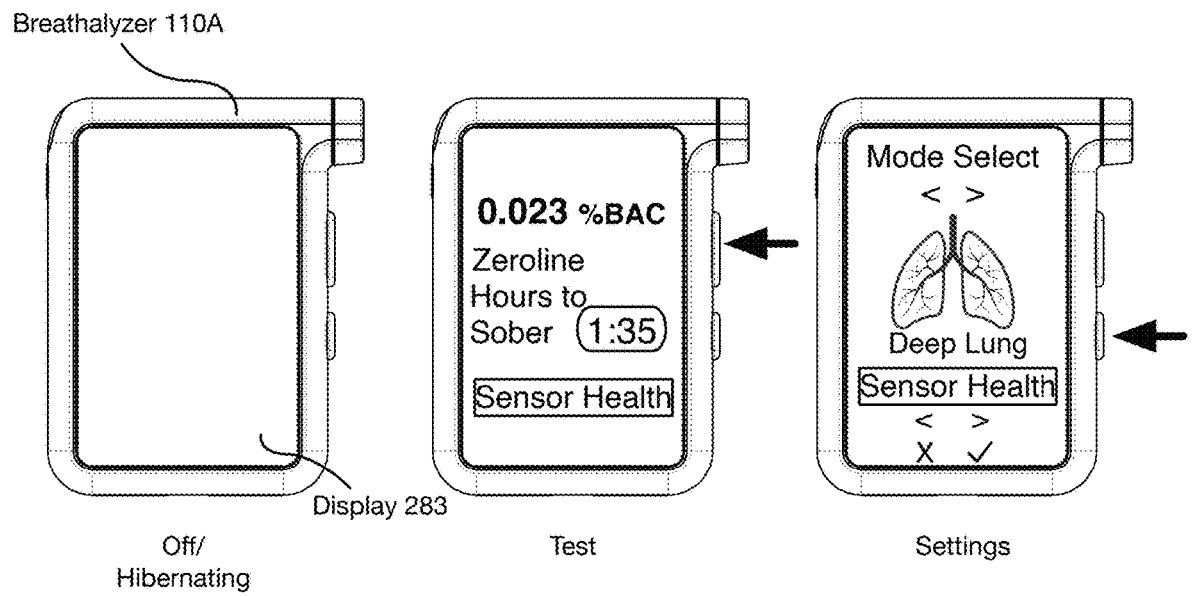
FIGS. 5A-5D depict views of an example of the sample receiving device shown in FIGS. 3A-3J.
Figure 5B:
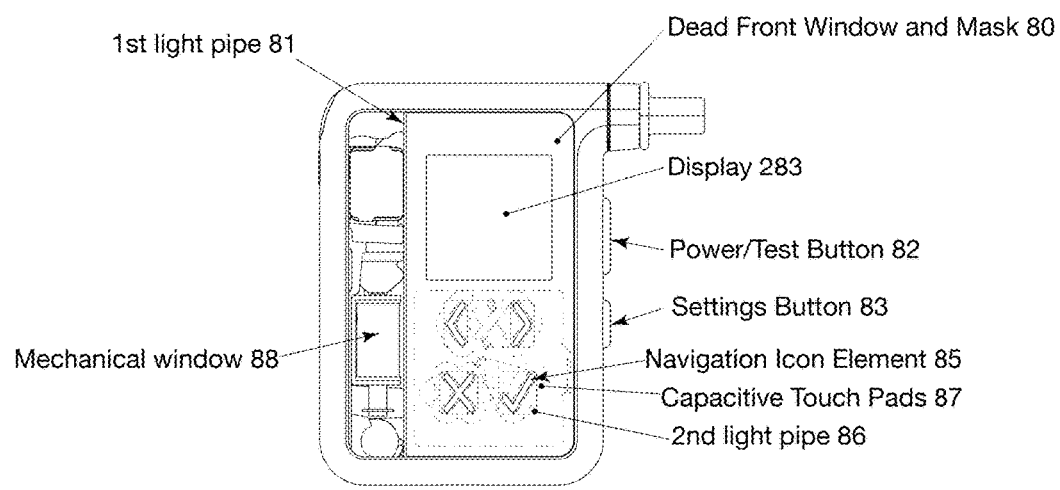

Views of the example of the breathalyzer shown in FIGS. 3A-3J are further depicted in FIGS. 5A-5D. FIG. 5A depicts operational states of the breathalyzer 110A, including an off/hibernating mode in which the dead-front display 283 appears to be inactive; a test mode in which the display depicts a BAC value for a recent breath sample provided by the user, an estimated duration of time by which the user will be sober, and an option to receive information regarding health of the alcohol sensor; and a settings mode, in which the user can select a mode by which to provide a breath sample, and an option to receive information regarding health of the alcohol sensor. FIG. 5B depicts a side view of the breathalyzer 110A, where the breathalyzer 110A includes: a first light emitting element (e.g., a first light pipe coupled to one or more light sources 89) 81 configured to provide indications of health of the alcohol sensor (e.g., by emitting different wavelengths of light corresponding to different health states of the alcohol sensor); a dead-front display 283 including a window with a mask 80; a power/test button 82; a settings button 83; a navigation icon element (e.g., mask) 85; a second light pipe 86 configured to light up the navigation icon element; a capacitive trace 87 structured for capacitive touch sensing; and a mechanical window 88.

Figure 5C:
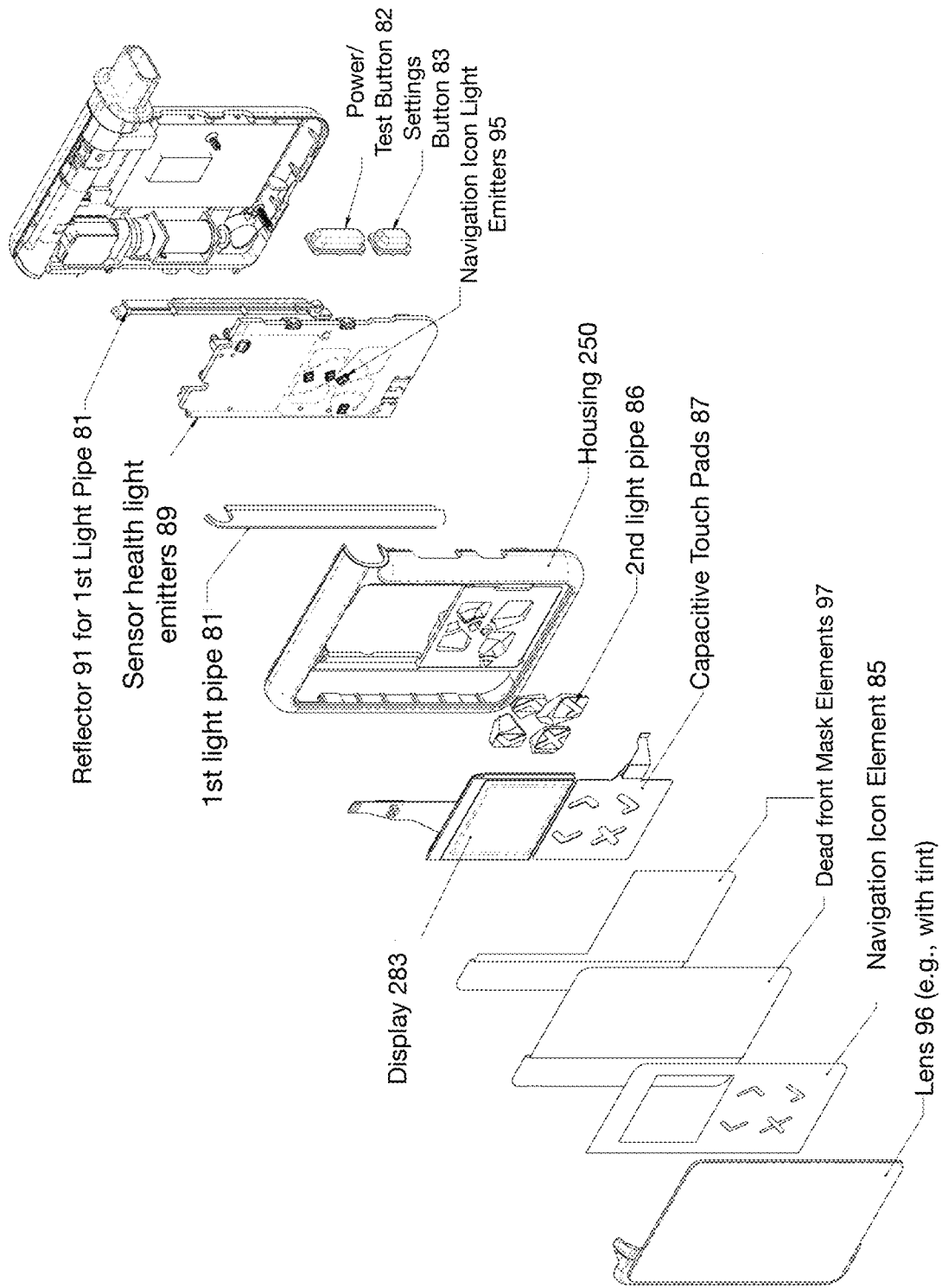

FIG. 5C depicts an exploded view of the breathalyzer 110A shown in FIGS. 5A and 5B, which further depicts: housing 250; a reflector 91 for the first light emitting element 81; light emitters 95 for the navigation icon element 85; a lens 96 for the display 283; and dead front display mask elements 97. The dead front display mask elements 97 can include a near-translucent gloss mask and a low transmission gloss mask, in order to improve a dead-front effect of the display 283. The lens 96 can be tinted (e.g., with a 20% optical tint, with a 30% optical tint, with a 40% optical tint, with a 50% optical tint, with a 60% optical tint, etc.).

Figure 5D:
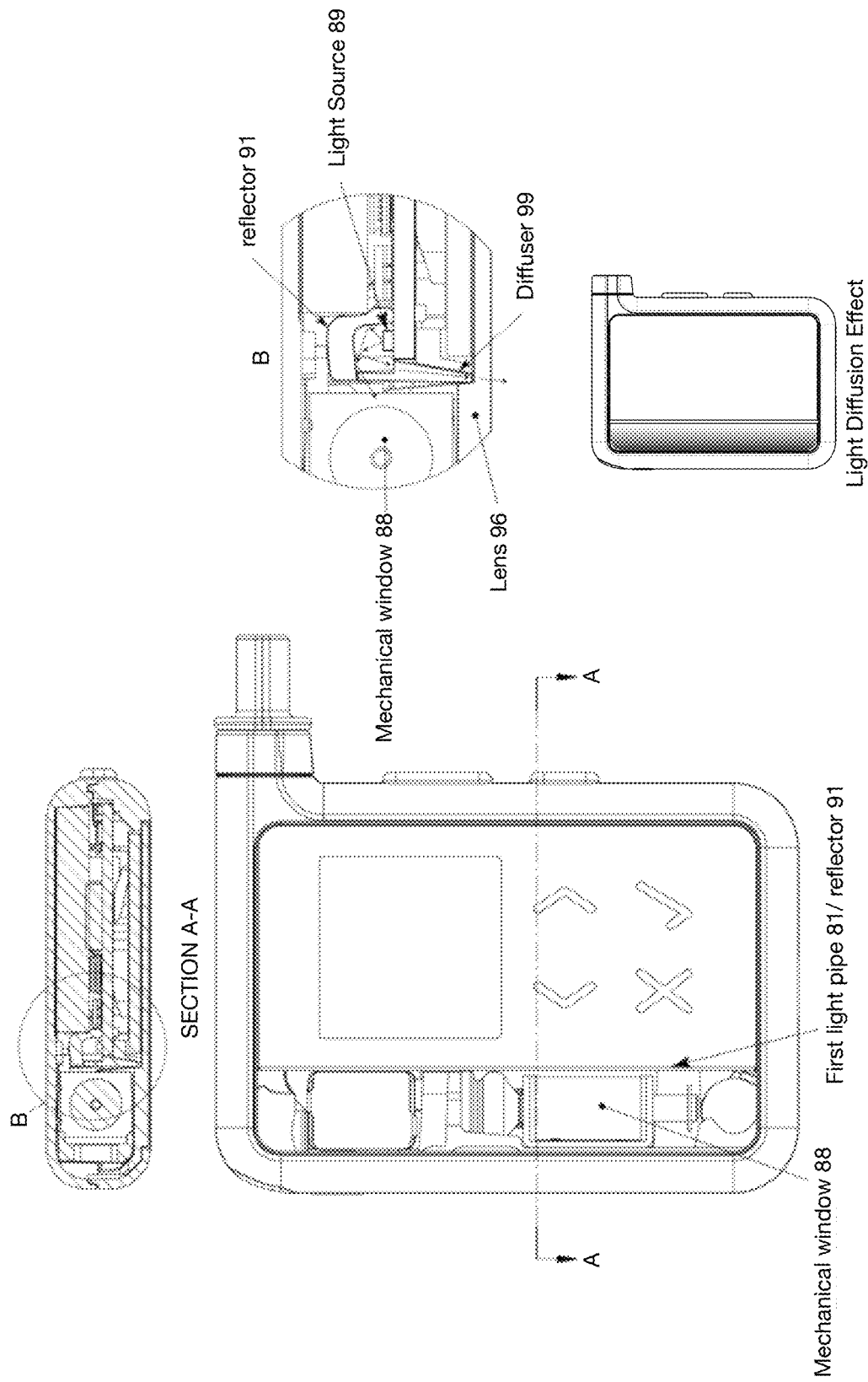

The first light emitting element 81 and reflector 91 can be arranged as a vertical bar that, with light sources 89, emit different wavelengths of light corresponding to different health states of the alcohol sensor. The first light emitting element 81 and reflector 91 are designed to provide thin lines on the lens 96, and illuminate the mechanical components in the mechanical window 88 in proximity to the first light emitting element 81 and reflector 91. As such, the light sources 89 are on the one side of the system, internal to the housing 250, and reflect around by way of the reflector 91 and diffuser 99 to illuminate both the light emitting element 81 and the mechanical window 88, as shown in FIG. 5D.

Figure 6:
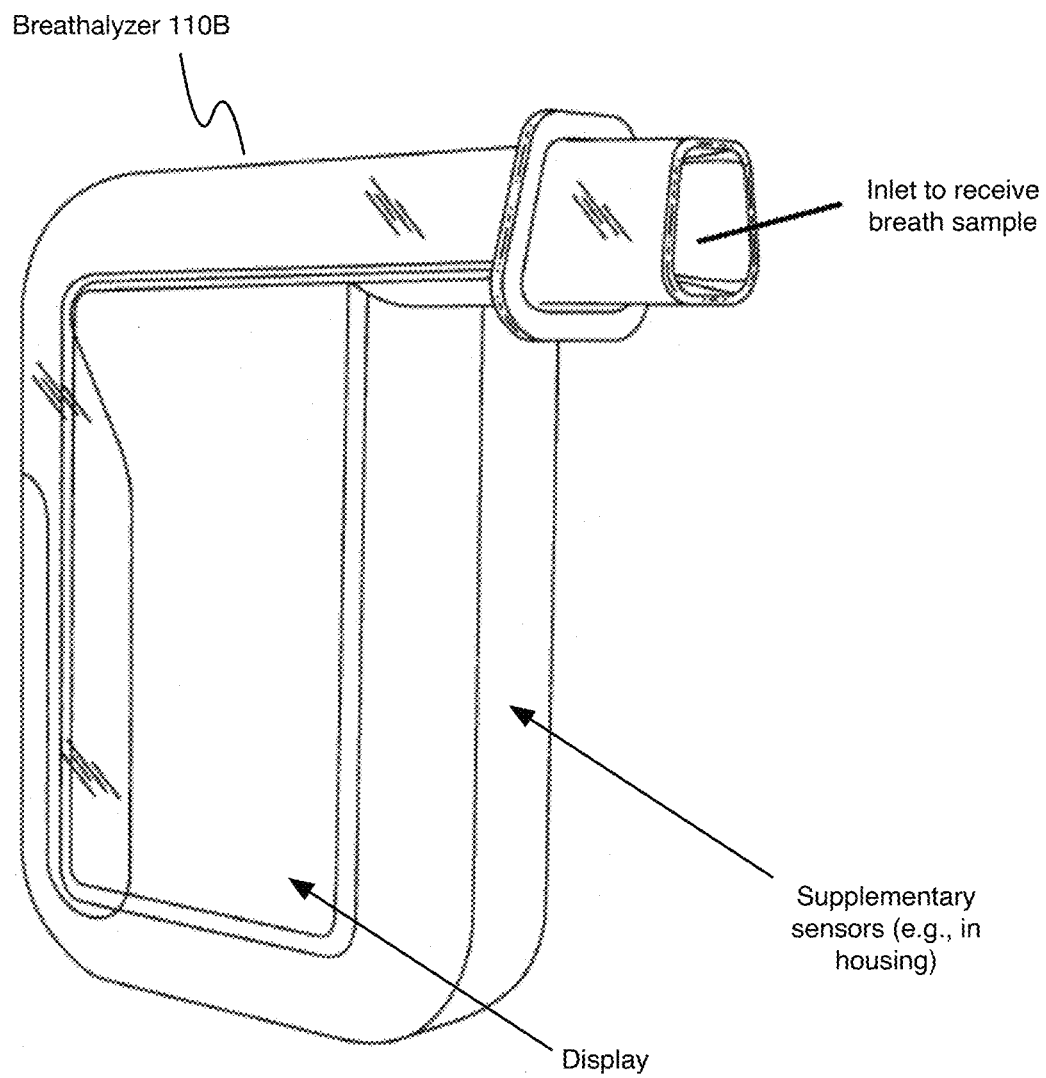
FIG. 6 depicts a first variant of an alcohol sensing device.
Figure 7:
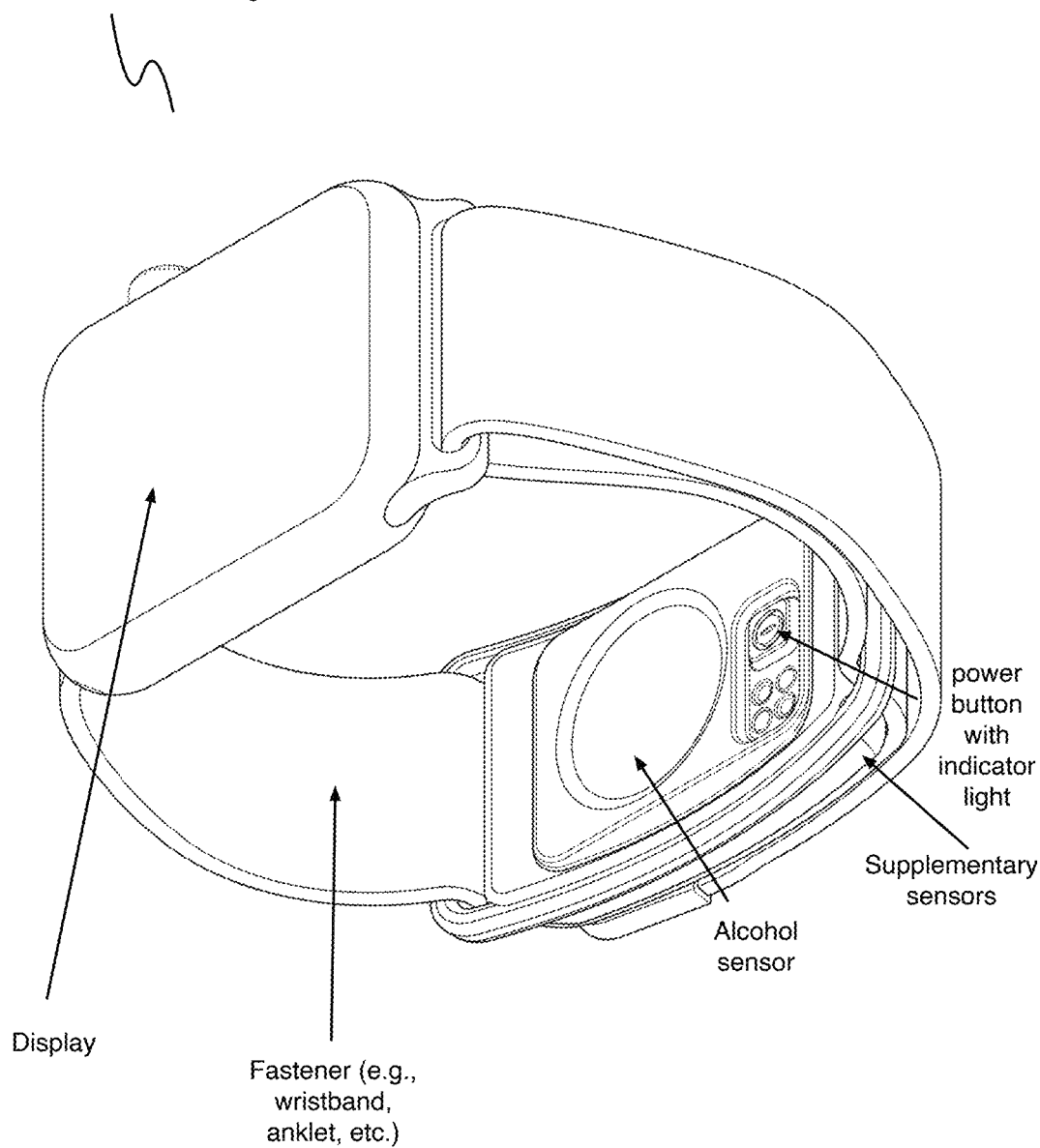
FIG. 7 depicts a second variant of an alcohol sensing device.

In a second set of variants, the alcohol sensing device includes a breathalyzer 110B (e.g., as shown in FIG. 6) configured to receive and analyze the alcohol content of breath samples from a user. In a third set of variants, the alcohol sensing device includes a transdermal device 110C (e.g., as shown in FIG. 7) configured to receive and analyze the alcohol content of perspiration collected (e.g., continuously collected) from a skin surface of the user.

The alcohol sensing device 110 preferably includes a set of one or more alcohol sensors 105 configured to collect biological samples (e.g., breath samples, transdermal samples, etc.) from a user (e.g., $1^{st}$ subset of data as described below). In preferred variants, the alcohol sensor includes a fuel cell sensor, but can additionally or alternatively include an enzymatic sensor, another sensor type, and/or any sensor described in any or all of the applications incorporated by reference above.

The system 100 preferably includes a set of supplementary sensors 120 configured to assess the health of the alcohol sensor value. Additionally or alternatively, the set of supplementary sensors 120 can function to assess a health of the supplementary sensors 120, a health of the overall device, and/or any other metrics. The set of supplementary sensors 120 preferably includes a temperature sensor, but can additionally or alternatively include any or all of: a humidity sensor, motion and/or orientation sensors (e.g., accelerometer), a clock, a location sensor, and/or any other sensor(s). The supplementary sensors 120 can be onboard the alcohol sensing device 110, offboard the alcohol sensing device (e.g., onboard a mobile user device 150), and/or distributed among any number of locations.

In some variants, the set of supplementary sensors 120 includes one or more accelerometers, which can function to detect shock and/or drop parameters (e.g., drop intensity, distance dropped based on free fall time, etc.) associated with the alcohol sensing device 110, which can function to detect if and/or how a device has been damaged or is predicted to have been damaged. This information can be used to affect (e.g., adjust, increase, decrease, correct, etc.) one or more sensor health metrics (e.g., sensor age, remaining number of sensor uses, etc.) based on accelerometer values (e.g., detected impact, severity of detected impact, type of impact, etc.). Additionally or alternatively, this information can be used to inform parameters of the one or more processors (e.g., increase sampling rate if device is moving around which indicates that the device is being used or is going to be used by the user [e.g., to collect an alcohol sample]), inform a timing of processing by the processor(s) 140 (e.g., if processor is in the middle of a computation the processor can trigger an error message to the user and/or initiate a redo of the computation since an impact can affect the computation results; processor can delay a computation until the device is stationary or relatively stationary; etc.). Further additionally or alternatively, the accelerometer values can be used to detect tampering (e.g., manipulation of the device, opening of the device, etc.) and/or for any other purpose(s).

The set of supplementary sensors 120 can optionally additionally or alternatively include one or more pressure and/or flow sensors, which can function to characterize a volume of air and/or flow rate of air that is entering a breathalyzer embodiment of the alcohol sensing device 110. This can function to ensure that an appropriate sample is being collected (e.g., above a minimum threshold flow rate, below a maximum threshold flow rate, etc.), that a breath sample is being collected (e.g., as opposed to air from a compressed air can if the user has an intention to tamper with his or her measurement), that a deep breath sample (e.g., air from the bottom of the lungs which can increase an accuracy of the alcohol measurement as compared with a shallow initial breath) is received, and/or can enable any other outcomes or benefits.

Additionally or alternatively, a pressure and/or flow rate sensor can be otherwise suitably used.

In some variants, the system utilizes sensors and/or information sources (e.g., applications, websites and/or web searching, etc.) to retrieve part or all supplementary information (e.g., humidity information), such as from a mobile user device as opposed to having all the sensors onboard the alcohol sensing device.

The system 100 preferably includes and/or interfaces with a set of processors (e.g., onboard the alcohol sensing device, onboard the mobile user device, at a cloud server, etc.), and further preferably one or more processors that act as a clock, maintaining an internal count (e.g., which can be verified each time the alcohol sensing device syncs with a mobile user device) that can be associated with measurements collected at the sensors. In preferred variants, the processor can tick every second, wherein this internal timing is used to attribute temporal values to other measurements, such that events (e.g., as described below) can be accurately time-stamped for later analysis.

The processors 140 can further function to retrieve one or more models, algorithms, sets of rules, lookup tables, and/or any other tools.

The system 100 preferably includes and/or interfaces with a power source, such as a battery, which functions to supply power for collecting and processing the set of data. At least a portion of the set of one or more batteries (e.g., rechargeable batteries) is preferably arranged onboard the alcohol sensing device. Additionally or alternatively, one or more power sources can be otherwise suitably arranged.

In a preferred set of variants, the alcohol sensing device 110 includes a set of batteries, wherein the set of batteries (e.g., individually, collectively, etc.) are partitioned into a normal use portion and a reserve portion (e.g., associated with a smaller amount of power storage), which can have different functionalities when used during a method 200. The normal use portion is preferably utilized to collect at least the $1^{st}$ subset of data and optionally a portion of the $2^{nd}$ subset of data (e.g., as described below), whereas the reserve portion is preferably utilized to collect any or all of the $2^{nd}$ subset of data. The reserve portion is preferably utilized when the alcohol sensing device 110 is in an otherwise "off" state (e.g., not collecting/unable to collect additional data in the $1^{st}$ subset, appearing as "off" to the user, not in communication with a mobile user device, etc.), wherein the reserve portion is only used to collect data in the $2^{nd}$ subset (e.g., data from a temperature sensor and/or other supplementary sensors 120). This can function to enable environmental information, which might correlate to events that are valuable to know regarding device health, to still be recorded even if alcohol data cannot be further collected (e.g., until a recharge), thereby enabling environmental information to be continuously collected (or collected for a large extended period) until the device has been recharged by the user.

In examples, the method 200 can include adjusting (e.g., decreasing) a sampling rate associated with data collection while operating with the reserve portion.

The system can include and/or interface with one or more user devices, such as one or more mobile user devices 150 (e.g., smartphones, tablets, laptops, etc.), which can: selectively communicate (e.g., sync) with the alcohol sensing device 110 (e.g., to receive data, to provide information, etc.); perform processing of any or all of data (e.g., at processors onboard the user device); initiate actions; and/or perform any other functions.

The system 100 can optionally be operable in and/or between a set of operation modes, which can function to inform any or all of the processes (e.g., initiated actions) in the method 200. The set of modes can include, but is not limited to, any or all of: a consumer mode (e.g., in which the user is testing his or her alcohol levels for personal use/interest); a volumetric mode (e.g., in which a minimum volume of air in a breathalyzer embodiment is checked for when collecting data in the $1^{st}$ subset); a deep pull lung mode (e.g., in which a set of minimum air volume thresholds and/or temporal thresholds and/or rate thresholds are utilized to ensure that human hallmarks corresponding to providing air from a bottom of their lungs is received); an evidential mode (e.g., in which a remote monitoring entity is receiving the data collected at the alcohol sensing device); and/or any other modes.

In a particular example of the deep pull lung mode, an algorithm is utilized in checking that a received breath sample is sufficient for further processing, which can include any or all of: checking for a minimum volume being received (e.g., 1 liter); analyzing the flow rate of the breath sample (e.g., over that minimum volume) to detect when the flow rate has decreased by a certain amount (e.g., to a predetermined percentage of the maximum flow rate, to indicate that the breath is rolling off which can correspond to the deepest air being received); checking a slope of the flow rate (a rate of change of the flow rate) to ensure that the user is still putting in an effort; checking for hallmarks (e.g., any or all of those described above) that a human is providing breath (e.g., not a machine) for tamper detection; and/or any other checks can be implemented. As such, the ability to process a deep lung sample can provide an estimate of actual BAC, where samples processed from breath of the mouth and the esophagus is often laden with alcohol from drinking, and therefore contains a higher alcohol concentration than BAC.

Additionally or alternatively, the system 100 can include and/or interface with any other components. System variations and operation modes of embodiments, variations, and examples of systems described are further provided below.

3.1 System—Variations

As shown in FIG. 1B, variations of a system 200 for monitoring intoxication of a user can include: a sampling subsystem 210 comprising a flow tube 220, an alcohol sensor 230 in communication with the flow tube 220, and a pump 240 configured to deliver breath samples from the user through the flow tube 220 and to the alcohol sensor 230.

The sampling subsystem 210 functions to facilitate delivery of a sample from a user, through the flow tube 220, and to an alcohol sensor 230, where the alcohol sensor 230 can then generate a signal in response to interacting with the sample from the user.

In embodiments, the flow tube 220 is included within a portion of the housing 250 described in more detail below. The flow tube 220 can be coupled to a mouthpiece 260 (also described below) that facilitates delivery of the sample of the user into the flow tube 220. The flow tube 220 can include an inlet 221 that is configured to facilitate sample inflow. The flow tube 220 is configured to interface with the alcohol sensor 230, where the alcohol sensor 230 is positioned downstream of the inlet 221. The flow tube 220 thus functions to facilitate transmission of a sample from the user to be analyzed by the processing subsystem 290. The flow tube 220 can be of unitary construction with the housing 250, can be physically coextensive with the housing 250, or can be coupled to the housing 250 (e.g., to an interior portion of the housing 250, to an exterior portion of the housing 250) in any other suitable manner. Similar to the housing 250, the flow tube 220 can also include a transparent or translucent portion that can be illuminated (e.g., by a lighting module) to provide an indicator function for the user.

The alcohol sensor 230 is preferably a fuel cell sensor that enables measurement of a user's blood alcohol content (BAC) or other measure of sample alcohol content by an electrochemical process. In particular, the fuel cell sensor is configured to produce an electrical current in response to oxidation of alcohol carried in a breath sample, wherein the magnitude of the produced electrical current varies in a predictable manner according to the amount (e.g., relative volume) of alcohol carried in the breath sample.

The alcohol sensor 230 can alternatively be a semiconductor sensor that produces a change in electrical resistance in response to an alcohol-dioxide reaction, wherein the magnitude of the change in resistance varies in a predictable manner according to the amount (e.g., relative volume) of alcohol carried in the sample from the user. In a specific example, the semiconductor sensor can incorporate tin-oxide as a sensing element; however, variations of the semiconductor sensor can alternatively use any other suitable sensing element. In other variations of the alcohol sensor 230, the sensor can include a spectrophotometer configured to produce a signal in response to absorbed or emitted light from alcohol molecules carried in the breath sample, or any other suitable type of sensor.

The pump 240 functions to drive at least a portion of the sample provided into the flow tube 220, toward the alcohol sensor 230. The pump 240 can also drive flow of at least a portion of the sample across the alcohol sensor 230. In variations, for a breath sample that is provided for a duration of time, the pump 240 can be configured to transition to a driving mode for only a portion of the duration of time, such that only a portion of the breath sample is driven across the alcohol sensor 230. In specific examples, an average breath sample volume provided into the flow tube 220 during a five second sample is about 5,000 mL. The first 3,500 mL can be disregarded because it comes from the mouth and esophagus, which often have a higher alcohol content than the actual BAC value of the user. As such, in specific examples, the pump 240 can be configured to transition to a driving mode to drive only a portion (e.g., final portion, final 1500 mL portion, final 1000 mL portion, final 500 mL portion, final 250 mL portion, etc.) of the breath sample across the alcohol sensor 230. This operation mode ensures that the breath sample provided to the alcohol sensor 230 arrives from one direction, which is important for accuracy, and also only allows air from the deepest part of the lungs to be tested for accurate measurement of BAC. As such, in variations, the pump 240 is configured to drive a portion of the sample (and omit driving a remainder of the sample) across the alcohol sensor 230, wherein the portion of the sample is associated with a deep lung volume of air from the user.

The pump 240 can be a solenoid pump. Alternatively, the pump 240 can be another type of air pump.

In variations, the pump 240 can be configured, with control elements of the system 200 described, to meter a stored sample across the alcohol sensor (e.g., in relation to temperature checks associated with threshold operating temperatures described below, in relation to clock checks associated with standard clearing times described below, etc.), such that the user can provide a breath sample at a first time point (e.g., when convenient for the user), and the breath sample can be processed when the alcohol sensor and system 200 are in suitable states (e.g., suitable temperature states, suitable time threshold states, etc.) for processing the sample.

As shown in FIG. 1B, embodiments, variations, and examples of the system 200 can include a housing 250 surrounding the sampling subsystem 210. The housing 250 is configured to enclose at least a portion of the system 200, and functions to protect elements of the system 200 over the lifetime usage of the system 200. In some embodiments, the housing 250 can further function to enhance portability of the system 200, such that the user can conveniently bring the sample receiving module wherever he/she goes. As shown in FIG. 1B, the housing 250 can support coupling of the flow tube 220 and the mouthpiece 260, described in more detail below, such that the mouthpiece 260 is reversibly coupled to the flow tube 220 and retained in place at an opening of the housing 210. The housing 250 can include a transparent or translucent portion that allows elements within the housing 250 to be visible or identifiable. Portions of the housing 250 that are transparent or translucent can also function to enable transmission of visually-observable information (e.g., optical signals, signals from displays, signals from light-emitting elements, etc.) from elements contained within housing 250, to observers outside of the housing 210. However, in other variations, the housing 250 can be substantially opaque to hide elements within the housing 250. The housing 250 is preferably composed of a polymer that is processed to define features of the housing 250 (e.g., by machining, by injection molding, by casting, by printing, etc.); however, the housing 250 can alternatively be composed of any other suitable material and processed by any other suitable process.

As shown in FIG. 1B, embodiments, variations, and examples of the system 200 can include a mouthpiece 260 coupled to the flow tube 220 of the sampling subsystem 210. The mouthpiece 260 functions to promote provision of a suitable sample into the flow tube 220. The mouthpiece 260 can also function to facilitate usage of the system 200 by multiple users (e.g., such that each user has their own respective mouthpiece 260 unit.

The mouthpiece 260 can be configured to mechanically couple (e.g., with protrusions/depressions, with slots, with keys, with tabs, with threads, by press fit, etc.) to the inlet 221 of the flow tube 220 and/or to a portion of the housing 250 that retains the flow tube 220 in position, in order to facilitate sample reception from the user. The mouthpiece 260 can be configured to permanently couple to the inlet 221 of the flow tube 220 and/or the housing 250, semi-permanently couple to inlet 221 of the flow tube 220 and/or the housing 250, or reversibly couple to inlet 221 of the flow tube 220 and/or the housing 250. In one specific example, the mouthpiece 260 is configured to be reversibly coupled to the inlet 221, such that the mouthpiece 260 is a disposable and replaceable element of the system 200.

Furthermore, the mouthpiece 260 can define unique identifiers (e.g., colors, textures, geometric features, etc.) that facilitate usage of the system 200 by multiple users. Additionally or alternatively, the mouthpiece 260 can include a near-field communication (NFC) element 261 with associated communication protocols by which the system 200 (e.g., alcohol sensing device and/or mobile communication device of the user, where the mobile communication device can pair with the alcohol sensing device) can detect that the mouthpiece 260 is a verified or authorized mouthpiece 260 that can be used with the system 200 for accurate processing of provided samples. As such, the mouthpiece can include a near-field communication (NFC) element that can be interrogated in order to determine if the mouthpiece is authorized for use with the sampling subsystem. The NFC element 261 can include inductive coupling elements (e.g., antennas) between NFC-enabled EVSE units and NFC-enabled user devices, operating according to ISO/IEC 18092/ECMA-340 standards, ISO/IEC 21481/ECMA-352 standards, ISO/IEC 14443 standards, FeliCa standards, or other standards.

Additionally or alternatively, the mouthpiece 260 can include a radio-frequency identification (RFID) element 262 with associated communication protocols by which the system 200 (e.g., alcohol sensing device and/or mobile communication device of the user, where the mobile communication device can pair with the alcohol sensing device) can detect that the mouthpiece 260 is a verified or authorized mouthpiece 260 that can be used with the system 200 for accurate processing of provided samples. The RFID element(s) 262 can include a transponder, a receiver, and a transmitter, where an RFID tag of the mouthpiece 260 is structured to transmit digital data in response to being triggered by an interrogation pulse of the system 200 (e.g., at the alcohol sensing device, at the user mobile device, etc.). RFID elements implemented can include passive tags that are powered by interrogating radio waves of readers, and/or active tags that are coupled to a power source (e.g., battery), with capability for greater range communications. RFID tags implemented can be read-only, or have read/write functionality. RFID systems associated with the check-in request of Step S110 can be passive reader active tag (PRAT) systems, active reader passive tag (ARPT), or active reader active tag (ARAT) systems. RFID systems can operate in low frequency bands (e.g., 120-150 kHz), high frequency bands (e.g., 13.56 MHz), ultrahigh frequency bands (e.g., greater than 100 MHZ), microwave bands (e.g., greater than 2000 MHZ), mm-wave bands, teraherz bands (e.g., as in teraherz frequency identification).

The systems described can further include NFC and/or RFID elements incorporated into the mouthpiece 260 and/or other system 200 components to satisfy tariff requirements, and/or to trigger operation modes of an application executing at the mobile device of the user. Exemplary operation modes can include one or more of: opening of the application (e.g., when the mouthpiece 260 is coupled with the flow tube 220, when an NFC/RFID element is positioned in proximity to a paired mobile computing device), initializing a sample test (e.g., when an NFC/RFID element is positioned in proximity to a paired mobile computing device, when the mouthpiece 260 is coupled to the flow tube 220, etc.), terminating a sample test (e.g., when an NFC/RFID element is positioned away from a paired mobile computing device, when the mouthpiece 260 is uncoupled from the flow tube 220, etc.), and/or other operation modes.

As shown in FIG. 1B, embodiments, variations, and examples of the system 200 can include a temperature sensor 270, which functions to sense device temperatures (e.g., of the alcohol sensing device), sample temperatures, and/or ambient temperatures from an environment surrounding the device, in relation to testing sessions using the system 200.

The temperature sensor 270 can be retained within the housing 250, in order to enable sensing of temperatures of components (e.g., flow tube 220 temperatures, alcohol sensor 230 temperatures, pump 240 temperatures, electronics temperatures, power source temperatures, etc.) of the system 200 that are inside the housing. Alternatively, the temperature sensor 270 can be positioned to sense temperatures (e.g., ambient environment temperatures) outside of the housing 250. Additionally or alternatively, the system 200 can include a set of temperature sensors that can measure temperatures of components inside the housing 250 and outside the housing 250. Additionally or alternatively, the temperature sensor(s) 270 can be positioned within other devices (e.g., mobile computing devices, other user devices) that can pair with (e.g., wirelessly pair with, pair with using a wired connection, etc.) or otherwise communicate with the sampling subsystem 210 and/or other components of the system 200. In some embodiments, temperature sensor(s) 270 of paired devices can be used to approximate system 200 temperatures described, upon determination of proximity between the paired devices and the sampling subsystem 210 and/or other components of the system 200.

In embodiments, variations, and examples, the temperature sensor(s) can include one or more of: thermistors (e.g., negative temperature coefficient thermistors, positive temperature coefficient thermistors, etc.), thermocouples, resistance temperature detectors (RTDs), semiconductor-based sensors, infrared (IR) sensors, microelectromechanical systems (MEMS) temperature Sensors, and/or other suitable temperature sensors.

Sensing temperatures can support operation modes of the system 200, described in further detail below.

As shown in FIG. 1B, embodiments, variations, and examples of the system 200 can include a first user interface 282, which functions to receive inputs, transmit inputs to other system 200 components, and provide information to the user in response to instructions executed by electronics of the system 200. The first user interface 282 can be integrated with an alcohol sensing device comprising the sampling subsystem 210, and as shown in FIG. 1B, a variation of the alcohol sensing device 110 can include an integrated user interface 282 including a display. The system 200 can also a second user interface 284, where the second user interface 284 can be integrated with a mobile computing device associated with the user (e.g., mobile phone, tablet, wrist-borne mobile computing device, etc.), where the mobile computing device can pair with the alcohol sensing device in coordination with alcohol testing events. As such, the system 200 can include a distributed user interface including the first user interface 282 and the second user interface.

The first user interface 282 and/or the second user interface 284 can include one or more of: a display, a touch sensitive display, a button, a dial, a microphone, a speaker, an audio output device, a haptic feedback device, a light emitting element, and/or any elements described in applications incorporated by reference above.

In relation to method steps described below, the first user interface 282 and/or the second user interface 284 can comprise a dead-front display lens 283 (an example of which is shown in FIGS. 5A-5C), which allows the first user interface 282 and/or the second user interface 284 to operate in a "stealth mode". The dead-front display lens 283 is structured to allow observation of displayed information only when back-lit. When operating in the "stealth mode", the system 200 can be configured to receive a sample (e.g., a breath sample) from the user and process the sample by way of the alcohol sensor 230, in order to return an alcohol content metric for the sample, with the first user interface 282 and/or the second user interface 284 operating in a discreet manner (e.g., without visibly displayed information, without audio output signals, without visual signals, etc.), such that the alcohol sensing device 110 does not appear to be active.

The first user interface 282 and/or the second user interface 284 can, however, be configured in other suitable manners.

As shown in FIG. 1B, embodiments, variations, and examples of the system can include: a processing subsystem 290 at least partially disposed within the housing 250 and comprising a clock 295, wherein the processing subsystem comprises instructions stored in non-transitory media that, when executed, perform one or more of the following steps: performing a first system integrity check with steps for evaluating a set of conditions of the alcohol sensor 230; a second system integrity check with steps for evaluating a set of calibration data generated for the alcohol sensor 230; a third system integrity check with steps for evaluating environmental exposure conditions of the system 200; a fourth system integrity check with steps for determining proper function of the pump 240; a fifth system integrity check with steps for evaluating malfunctioning of the processing subsystem 290 and/or the alcohol sensor 230; and a sixth system integrity check with steps for evaluating a deviation between an actual alcohol sensor signal morphology and an expected alcohol sensor signal morphology (e.g., under ambient conditions). Aspects of system configurations and methods performed using embodiments of the systems 100, 200 and/or other system components are further described in detail below.

Performing the first system integrity check can involve verifying electrical coupling of the alcohol sensor 230 (e.g., to other electronics components of the system 200), such that the set of conditions includes an electrical coupling condition. In an example, verifying electrical coupling of the alcohol sensor 230 involves steps for testing capacitance (e.g., exercising a dual-layer capacitance) of the alcohol sensor 230 (in embodiments where the alcohol sensor 230 is a fuel cell sensor), in order to confirm that the alcohol sensor 230 is still suitably coupled to other electronics components of the system 200. For other sensor types, verifying electrical coupling of the alcohol sensor 230 can include applying test electrical signals (e.g., in relation to applied currents, applied voltages, etc.), and measuring an electrical signal (e.g., current signal, voltage signal, resistance, other signal) associated with the alcohol sensor.

Performing the first system integrity check can involve determining an age of the alcohol sensor 230, such that the set of conditions includes a sensor age condition. Determining an age of the alcohol sensor 230 functions to determine if the age of the alcohol sensor 230 is above a threshold age, such that results generated would be invalid or inaccurate. Determining the age of the alcohol sensor can include tracking or otherwise determining one or more of: a number of uses of the alcohol sensor 230 (e.g., in relation to number of testing events); an age of the alcohol sensor 230 determined from a manufacture time point to a current time point; an age of the alcohol sensor 230 determined from a date of first use to a current time point; an estimated age of the alcohol sensor 230 determined from an initial time point (e.g., time of first use, time of manufacture, etc.), historical data capturing ambient conditions of use of the alcohol sensor, number of uses of the alcohol sensor in relation to testing events, and/or other factors; and determining age in another suitable manner.

Performing the second system integrity check with steps for evaluating a set of calibration data generated for the alcohol sensor 230 functions to determine if calibration data associated with calibration of the alcohol sensor 230 is corrupted or otherwise invalid, if the system 200 is due for calibration, and/or if the system 200 is overdue for re-calibration. Evaluating the set of calibration data can involve performing a calibration operation with a zero alcohol sample (e.g., a breath sample provided by the user, where the user has not consumed alcohol or any substance that would otherwise produce a non-zero alcohol content value during testing). The calibration operation can be performed using systems and/or according to method steps described in U.S. application Ser. No. 15/492,216 filed on 20 Apr. 2017, which is herein incorporated in its entirety by this reference.

In relation to the second system integrity check, determining if the system 200 is due for calibration or overdue for re-calibration can include tracking or otherwise determining one or more of: a time point of a prior calibration event; a number of calibration events performed over the lifetime of use of the system 200; a change in ambient conditions associated with the system 200; a change in device status associated with the system 200; a determination of a period of disuses of the system 200; a determination of a period of disuse of the system 200 followed by a period of use of the system 200; a number of uses of the alcohol sensor 230 (e.g., in relation to number of testing events); an age of the alcohol sensor 230 determined from a manufacture time point to a current time point; an age of the alcohol sensor 230 determined from a date of first use to a current time point; an estimated age of the alcohol sensor 230 determined from an initial time point (e.g., time of first use, time of manufacture, etc.), historical data capturing ambient conditions of use of the alcohol sensor, number of uses of the alcohol sensor in relation to testing events, and/or other factors; and other suitable parameters associated with calibration of the system 200.

Performing the third system integrity check with steps for evaluating environmental exposure conditions of the system 200 functions to determine if the alcohol sensing device 110 has been exposed to extreme conditions (e.g., extreme temperature conditions, extreme humidity conditions, extreme pressure conditions, extreme mechanical forces, etc.) and/or any conditions outside of specified storage conditions. Performing the third system integrity check can include interrogating one or more sensors of the set of supplementary sensors (e.g., temperature sensors, pressure sensors, humidity sensors, accelerometers, light sensors, etc.) described, and comparing conditions represented in data resulting from interrogation, to threshold conditions indicative of exposure to extreme conditions. In examples, a threshold temperature condition can be a temperature greater than 90F, greater than 95F, greater than 100F, greater than 110F, greater than 120F, or greater. In examples, a threshold pressure condition can be a temperature greater than 15 PSI, 18 PSI, 20 PSI, 22 PSI, 24 PSI, 26 PSI, 28 PSI, 30 PSI, or greater. In examples, a threshold humidity condition can be a humidity greater than 90% relative humidity, 95% relative humidity, or greater.

Performing the fourth system integrity check with steps for determining proper function of the pump 240 functions to determine if the pump 240 is electrically connected and functioning properly. In an example, verifying electrical coupling of the pump 240 involves steps for testing voltage across the pump 240, in order to confirm that the pump 240 is still suitably coupled to other electronics components of the system 200. For other sensor types, verifying electrical coupling of the pump 240 can include applying test electrical signals (e.g., in relation to applied currents, applied voltages, etc.), and measuring an electrical signal (e.g., current signal, voltage signal, resistance, other signal) associated with the pump 240. Determining proper function of the pump 240 can also involve performing a test run of the pump 240 (e.g., with verification that the pump is pressurizing and/or depressurizing as expected).

Performing the fifth system integrity check with steps for evaluating malfunctioning of the processing subsystem 290 and/or the alcohol sensor 230 functions to determine if previous sample tests have resulted in critical errors that indicate that the algorithm by which the alcohol sensing device 110 operates is malfunctioning, and/or any sensors of the system 200 are malfunctioning. Performing the fifth system integrity check can include evaluating a log of prior sample test data to determine if any errors have been detected and not resolved. Performing the fifth system integrity check can then include resolving any detected errors or malfunctions, and/or notifying the user or another entity that the alcohol sensing device 110 is not operating properly and should be replaced.

Performing the sixth system integrity check includes steps for evaluating a deviation between an actual alcohol sensor signal morphology and an expected alcohol sensor signal morphology (e.g., under ambient conditions). Performing the sixth system integrity check can involve a cloud-based analysis of raw data from previous test results involving the alcohol sensing device 110. The cloud-based analysis can be performed upon pairing the alcohol sensing device 110 with a mobile computing device (e.g., a mobile computing device associated with the user), which has a link to a cloud-based computing processor for analyzing the alcohol sensor signal. Alternatively, the cloud-based analysis can be performed with a direct link between the alcohol sensing device 110 and the cloud-based computing processor. Still alternatively, the sixth system integrity check can be performed on-board the alcohol sensing device, in embodiments wherein the alcohol sensing device includes edge-deployed sensors and processors (e.g., neural processing units) capable of performing the analysis. Performing the sixth system integrity check can include determining if the alcohol sensor signals fit an expected shape. In a specific example, performing the sixth system integrity check can include curve fitting alcohol sensor signals against an ideal anatomy of the signal (e.g., under ambient conditions, under standard temperature, under standard pressure, under another suitable standard condition), where the ideal anatomy of the signal can take the form of equation [1] below:

$$f(x)=a*(e^{(-b*x)}-e^{(-(b/c)*x)}) \qquad [1]$$

In the specific example, performing the sixth system integrity check can then include determining significant deviations of the alcohol sensor signal from the expected signal shape (e.g., based upon determination of coefficients of equation [1] in comparison to threshold values for such coefficients]. Performing the sixth system integrity check can then include resolving any issues associated with unexpected signal shapes (e.g., re-calibrating the alcohol sensor, etc.), and/or notifying the user or another entity that the alcohol sensing device 110 is not operating properly and should be replaced. The variations of the sixth system integrity check can additionally or alternatively be performed using systems and/or according to method steps described in U.S. application Ser. No. 15/492,216 filed on 20 Apr. 2017, which is herein incorporated in its entirety by this reference.

The processing subsystem 290 can also include instructions stored in non-transitory media that, when executed, perform: prompting the user to provide a breath sample to the alcohol sensing device upon satisfaction of one or more of: the first system integrity check, the second system integrity check, the third system integrity check, the fourth system integrity check., the fifth system integrity check, sixth system integrity check, and/or other system integrity checks.

In relation to the system 200 and the processing subsystem 290, the alcohol sensing device 110 can be configured to be always on, as long as the power source has sufficient power to power the system 200. As such, the clock 295 enables the system 200 and processing subsystem 290 to retain a sense of time and to determine when a prior sample was processed by the alcohol sensor 230, in comparison to other alcohol sensing devices that do not retain a sense of time between sample testing events. Such systems that do not retain a sense of time thus must automatically require a standard clearing time (given that there is no ability to determine when a prior sample was received), before receiving another sample in order to ensure testing accuracy, where the standard clearing time ensures clearing of the alcohol sensor 230 such that it can be used to accurately test a new sample. The standard clearing time can be a duration of up to 30 seconds, up to 1 minute, up to 1.5 minutes, up to 2 minutes, up to 2.5 minutes, up to 3 minutes, up to 3.5 minutes, up to 4 minutes, up to 4.5 minutes, up to 5 minutes, up to 5.5 minutes, up to 6 minutes, up to 6.5 minutes, up to 7 minutes, up to 7.5 minutes, up to 8 minutes, up to 8.5 minutes, up to 9 minutes, or greater than 9 minutes.

In variations, the processing subsystem 290 can thus further be configured for one or more of: receiving a temperature dataset from the temperature sensor 270, comparing a temperature metric to a threshold condition upon processing the temperature dataset, determining a time duration from a time point of testing of a previous breath sample received at the sampling subsystem, and transmitting instructions for prompting the user to provide a breath sample according to a testing protocol, wherein the testing protocol is modified based upon the temperature metric and the time duration. Given that the system 200 retains a sense of time, modification of the testing protocol can include prompting the user to provide a breath sample without requiring the user to unnecessarily wait according to a standard clearing time requirement, upon determination that a duration of time has passed after the system 200 has processed a prior sample, and the duration of time satisfies the standard clearing time requirement. In a specific example, the processing system 290 can determine that a prior sample was received and processed 6 minutes before a current time point, which satisfies the standard clearing time requirement. The user can thus be prompted to provide a sample for processing without unnecessarily waiting an additional duration of time (e.g., a minimum wait time for sensor clearing has been exceeded). Such elements of the system 200 can thus streamline and improve rapidness of user testing, whereby, in many situations, the user can, whenever the user desires or is prompted, provide a sample and receive test results within an unprecedented duration of time. The duration of time can be less than 30 seconds, less than 25 seconds, less than 20 seconds, less than 19 seconds, less than 18 seconds, less than 17 seconds, less than 16 seconds, less than 15 seconds, less than 14 seconds, less than 13 seconds, less than 12 seconds, less than 11 seconds, less than 10 seconds, or less.

Aspects of system configurations and methods performed using embodiments of the systems 100, 200 and/or other system components are further described in detail below.

Variations of the systems 100, 200 can further include a beacon device 272, which can function to enable location tracking of the alcohol sensing device 110 and/or other components of the systems 100, 200. The beacon device 272 can include Apple™ device, Android™ device, and/or other tracking device authorized components that support tracking of the alcohol sensing device 110 and/or other components of the systems 100, 200 using associated mobile computing devices (e.g., using Apple™ Find My technology support). The beacon device 272 can facilitate automatic triggering of actions (e.g., based upon a detected location of the user or other event). In an example, the beacon device 272 can trigger automatically prompting testing of the user, when the user is detected to enter, be in proximity to, or leave a location where alcohol is served. In another example, the beacon device 272 can trigger automatically prompting testing of the user, when the user is detected to access a vehicle (e.g., a vehicle paired with the alcohol sensing device through a wireless connection or through a wired connection, a vehicle paired with a mobile device of the user, etc.). As such, variations of the systems described can interact with beacon systems (e.g., Apple™ Beacon technology, Android™ Beacon technology, iBeacon, Estimote systems, etc.) in order to perform background functions, even when mobile applications associated are in an inactive state. In one example, the systems described can be configured to enable background operations of the system in line with the methods described, whenever the system interacts with a beacon system (e.g., if an iOS of an Apple device detects an iBeacon system). In an example operation of such a system, upon detection of a beacon system (e.g., using a BlueTooth LE advertising packet that facilitates invoking of devices when specific beacon types are detected), an individual can be prompted to turn on the breathalyzer device and/or select a notification on a mobile application associated with the breathalyzer device. Then, the breath sample provision process could be initiated within the application in a streamlined process. The beacon system can be associated with a specific environment.

Relatedly, the systems 100, 200 can implement on-board audio output devices, haptic feedback devices (e.g., with vibration capability) to emit an audible and/or vibration signal to help a user located a lost or misplaced alcohol sensing device, when the alcohol sensing device is paired with a mobile computing device supporting beacon-based tracking. Relatedly, the systems 100, 200 can further include a GPS device that enables location tracking for the alcohol sensing device 110.

Variations of the system 200 described can include other elements, such as electronics subsystem elements (e.g., comprising power sources, comprising signal pre-processing elements, comprising other circuitry, comprising on-board computing architecture, communications architecture, etc.), an accelerometer 274 (e.g., for mechanical force detection), a pressure sensor, a humidity sensor, or other elements some of which are described in Applications incorporated by reference above and below.

4. Method 200

As shown in FIG. 2A, an embodiment of a method 300 includes collecting data at an alcohol sensing device S310; detecting and analyzing a set of events associated with the set of data S320; and initiating a set of actions based on the set of events S340. Additionally or alternatively, the method 200 can include any or all of: selectively storing information S330, any or all of the processes described in U.S. application Ser. No. 14/169,029, filed 30 Jan. 2014; U.S. application Ser. No. 14/602,919, filed 22 Jan. 2015; U.S. application Ser. No. 14/631,125, filed 25 Feb. 2015; U.S. application Ser. No. 15/375,801, filed 12 Dec. 2016; U.S. application Ser. No. 15/492,216, filed 20 Apr. 2017; U.S. application Ser. No. 16/362,444, filed 22 Mar. 2019; and U.S. application Ser. No. 17/033,501, filed 25 Sep. 2020; U.S. application Ser. No. 17/574,278, filed 12 Jan. 2022; and U.S. application Ser. No. 18/109,720, filed 14 Feb. 2023; each of which is incorporated in its entirety by this reference, or any other suitable processes performed in any suitable order. The method 200 can be performed with a system as described above and/or any other suitable system.

The method 300 preferably functions to determine and maintain an accurate understanding of the health of its sensors, which can optionally be used for any or all of: providing maintenance and/or replacement and/or preservation information to a user; correcting any or all measurements recorded by the alcohol sensing device; adjust one or more operational parameters of the alcohol sensing device (e.g., sampling rate, mode, etc.) based on the sensor health information; enable improvement of the sensor health; increase a lifespan of the alcohol sensing device; and/or any other outcomes.

The method 300 can optionally be performed in accordance with one or more operating modes, where the different operating modes can be associated with different use cases (e.g., personal use vs. criminal justice use), different users, different goals, and/or any other parameters. The set of modes can include, but is not limited to, any or all of the modes described above.

Additionally or alternatively, the method 200 can include any other processes and/or perform any other suitable functions.

4.1 Method—Collecting Data at an Alcohol Sensing Device S110

The method 300 can include collecting data at an alcohol sensing device S110, which functions to receive information with which to perform any or all future processes of the method 300. Additionally or alternatively, the method 300 can include receiving data from another source (e.g., user device, $3^{rd}$ party information source, database, etc.) and/or any other process(es).

S310 is preferably performed at least initially in the method 300, but can additionally or alternatively be performed at another time or times during the method 300, multiple times (e.g., continuously throughout the method, at a predetermined frequency, etc.) during the method 300, and/or at any other time(s).

The set of data preferably includes at least a $1^{st}$ and $2^{nd}$ subset of data, but can additionally or alternatively include other subsets of data, a single type of data, and/or any other data.

The $1^{st}$ subset of data includes a set of alcohol measurements (e.g., alcohol amount in a sample [e.g., breath sample, transdermal sample, etc.]) from one or more alcohol sensors of the alcohol sensing device. In a preferred set of variants, for instance, the set of alcohol measurements includes a set of alcohol values from a fuel cell sensor of the alcohol sensing device. In alternative variants, the alcohol values can be collected from an enzymatic sensor or any other alcohol sensor of the device.

The $2^{nd}$ subset of data includes a set of supplementary measurements from one or more supplementary sensors of the alcohol sensing device. The set of supplementary measurements preferably includes at least temperature measurements from one or more temperature sensors, but can additionally or alternatively include humidity (e.g., moisture, dryness, etc.) measurements from one or more humidity sensors; time measurements from an internal clock; flow rate measurements from a flow rate sensor; pressure measurements from a pressure sensor; location data from one or more location (e.g., GPS) sensors; and/or any other measurements. Additionally or alternatively, any other measurements, additional or alternative to those described above, can be received.

Additionally or alternatively, any or all of the supplementary measurements can be retrieved from offboard the alcohol sensing device, such as from a mobile user device, an internet source, a database (e.g., cloud storage), memory, and/or any other sources. In some variants, for instance, humidity data can be retrieved (e.g., in response to a trigger, in response to the temperature value exceeding a predetermined threshold, etc.) from a wirelessly connected mobile user device and/or database (e.g., based on location information collected on the user device and/or alcohol sensing device, based on humidity data collected onboard the mobile user device, etc.). This can prevent the need for a costly (e.g., in computation, in financial cost, in space, etc.) humidity sensor to be onboard the alcohol sensing device.

The $1^{st}$ and $2^{nd}$ subsets of data can be collected at the same times (e.g., at the same intervals, according to the same sampling frequency, etc.) relative to each other (e.g., for variants in which transdermal alcohol is sensed continuously), at different times (e.g., according to different sampling frequencies, wherein the $2^{nd}$ subset is taken in absence of the $1^{st}$ dataset, wherein the $1^{st}$ subset is collected in response to user initiation and the $2^{nd}$ subset is collected at a predetermined set of intervals, etc.) relative to each other, and/or at any combination of overlapping and non-overlapping times.

Figure 8:
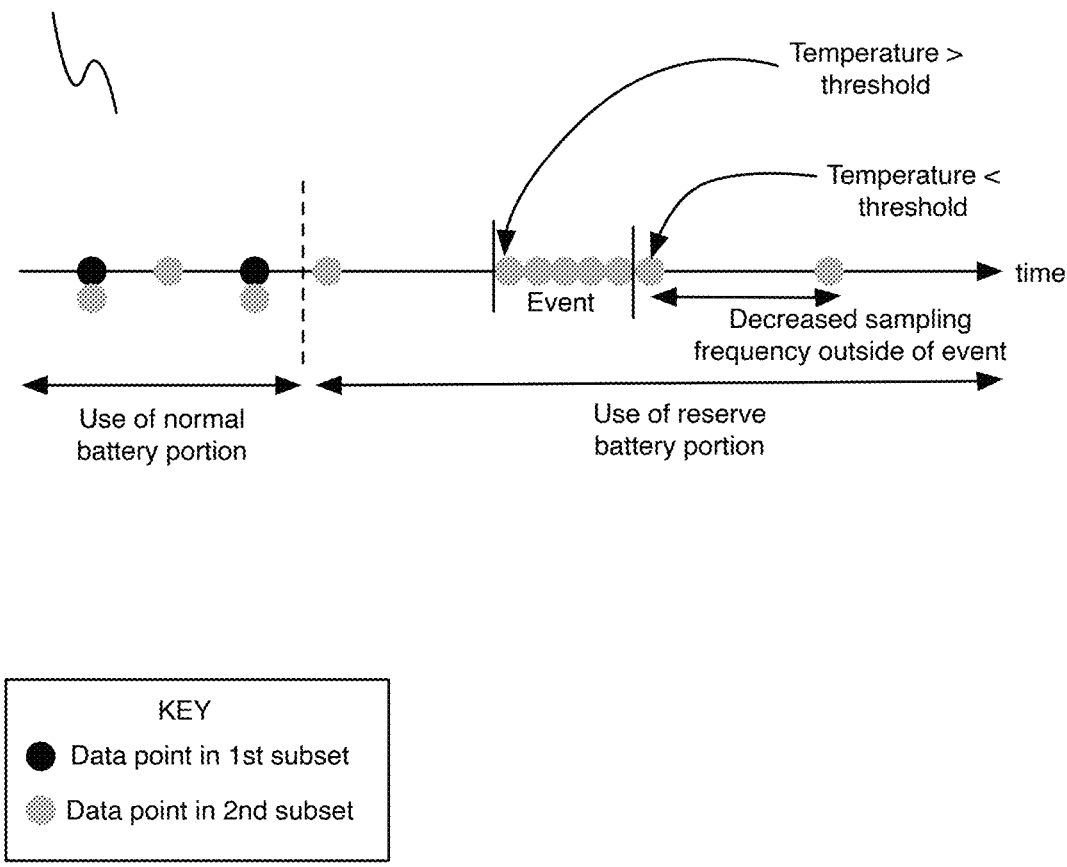
FIG. 8 depicts a variant of data collection during a method for detecting and maintaining performance of an alcohol sensing device.

The $2^{nd}$ subset of data is preferably collected at least partially in accordance with the detection of an event (e.g., as described below, as shown in FIG. 8, etc.). For instance, upon detecting the start of an event, a sampling frequency of the $2^{nd}$ subset of data is preferably increased (e.g., until detecting an end of the event). This can function to enable higher resolution data to be recorded surrounding events, which are associated with more actionable insights than non-event data.

In some variants, any or all of the data is collected (e.g., sampling rate determined/adjusted) at least partially in accordance with one or more power source parameters, such as a level of remaining battery (e.g., normal use battery portion, reserve use battery portion, etc.). For instance, in preferred variants, in an event that a normal use battery portion is drained but a reserve use battery portion is available, collection of the $1^{st}$ subset of data can cease whereas collection of the $2^{nd}$ subset of data remains (e.g., at the same sampling frequency, at a reduced sampling frequency, depending on event detection, etc.).

Additionally or alternatively, S110 can include any other process(es) and/or be performed in any other suitable way.

4.2 Method—Detecting and Analyzing a Set of Events Associated with the Set of Data S120

The method 300 can include detecting and analyzing a set of events associated with the set of data S320, which can function to: monitor for progressive sensor decline, detect events considered to be catastrophic (e.g., requiring replacement rather than maintenance of the sensors), differentiate between event types, and/or perform any other functions.

S320 is preferably performed in response to S310, but can additionally or alternatively be performed at any other suitable times.

An event preferably refers herein to an occurrence and/or duration for which the environmental conditions associated with the alcohol sensing device are determined or predicted to affect the health (e.g., functionality, effective age, etc.) of the alcohol sensing device (e.g., health of the alcohol sensor), which can in turn affect the accuracy of its measurements, the confidence associated with the measurements, and/or any other outputs. Events can range from progressive decline (e.g., based on routine usage of the device, based on lack of usage of the device, etc.) to catastrophic damage (e.g., device left in a hot car for a week).

The events, and any values associated with the events (e.g., start time, end time, duration, measurements characterizing the event(s), etc.), are preferably detected based on the $2^{nd}$ subset of data, but can additionally or alternatively be detected based on the $1^{st}$ subset of data, a combination of subsets of data, and/or any other information. In a preferred set of variants, sensor health events are detected based on least on temperature data in the $2^{nd}$ subset. Additionally or alternatively, sensor health events can be detected based on other supplementary data, based on the $1^{st}$ subset of data, and/or based on any other information.

Detecting the start of an event preferably includes comparing any or all of the $2^{nd}$ subset of data with a set of thresholds. For instance, in a first set of variants, an event is detected based on comparing a temperature measurement with a predetermined temperature threshold, wherein an event is initiated in an event that the temperature measurement exceeds the threshold. Additionally or alternatively, multiple thresholds can be used, wherein a severity of the event (e.g., routine vs. moderate vs. catastrophic) is characterized based on which threshold(s) the measurement exceeds. Further additionally or alternatively, events can be detected and/or characterized based on temperatures falling below a threshold (e.g., indicating device has been in freezing temperatures), based on other data (e.g., humidity measurements, aggregated data, etc.), and/or with any other tools (e.g., trained algorithms, machine learning models, equations, etc.).

Temperature can be an important metric to assess sensor health, such as in the case of using fuel cell sensors, as high temperatures can cause the fluid (e.g., water) in the sensor to evaporate, drying out the sensor and preventing or reducing the ion membrane's ability to function. Further, it can be challenging to re-introduce fluid into the sensor once it is gone, as the wafer can be hydrophobic. Humidity can be further be an important metric, because at high humidity, less fluid can evaporate.

Additionally or alternatively, other damaging events can be detected. For instance, accelerometer measurements can be collected and analyzed to detect, characterize, and/or quantify damage to the alcohol sensing device.

Additionally or alternatively, events that positively or neutrally affect sensor health can be detected, such as usage of the alcohol sensor. In examples, for instance, if an alcohol sensor has been degraded due to drying out, detecting that a user has used (e.g., blown into, provided perspiration, etc.) the alcohol sensor, and thereby applied moisture to it, can be used to update the sensor's health value (e.g., decrease its level of degradation, increase its health level, decrease its effective age, decrease the amount that a drying out event contributes to sensor degradation, etc.).

In a particular example, a catastrophic event corresponding to the device having been left in a hot car for a week can be detected upon comparing a temperature measurement collected at the alcohol sensing device with a predetermined threshold. An event such as this can be deemed severe (e.g., catastrophic) for devices of any kind or age (e.g., brand new, 5 years old, etc.), as such heat can completely dry out the sensor. As such, commensurate actions can be triggered later in the method 200 (e.g., alerting user that the alcohol sensor needs to be replaced, providing proper storage instruction reminders to the user, not allowing further alcohol measurements from the device to be used [e.g., to operate a vehicle, to be used in criminal justice applications, etc.], and/or collected, etc.).

Detecting the initiation of an event and/or a suspected event can optionally trigger the collection, retrieval, and/or analysis of other data, which can be used for instance to: confirm the event, characterize the event, and/or otherwise be suitably used. For instance, in an event that the temperature exceeds a threshold, a humidity measurement (and/or retrieval of humidity data from another source) can be triggered, which can function to correct for the temperature value and/or otherwise be used to categorize the event. In specific examples, a humidity value can be used to further characterize a detected event. For instance, a high detected temperature associated with humidity above a threshold can degrade a sensor less than a high detected temperature associated with humidity below a threshold, which is more drying.

Additionally or alternatively, any other metrics can be detected, temperature and humidity can be aggregated (e.g., according to an algorithm, model, and/or equation, etc.), and/or any other data can be utilized in any suitable ways.

S320 can optionally trigger one or more data collection triggers in S320, such as, but not limited to: increasing a sampling rate upon detection of an event, initiating the storage (e.g., in S330) and/or transmission of data during an event, and/or any other actions.

S320 preferably includes assessing a health of the alcohol sensor during and/or in response to the event, which functions to assess the effect of the event on the alcohol sensor. Assessing the health preferably includes calculating a set of health metrics, which can be determined with any or all of: a set of algorithms (e.g., trained, untrained, etc.), set of models (e.g., machine learning model, neural network, etc.), equation(s), decision tree(s), lookup table(s), and/or any other tools. In variants including a set of algorithms and/or models, the algorithms and/or models can be: specific to the user (e.g., trained and/or tuned specifically for the user), specific to a subgroup (e.g., location subgroup, demographic subgroup, mode subgroup, etc.) associated with the user, generic to all users, and/or otherwise suitable to the user or users.

The set of health metrics preferably quantify an effective age of the alcohol sensor, but can additionally or alternatively: quantify a number of times that the alcohol sensor can be used, quantify a progress of the alcohol sensor toward a needed intervention (e.g., replacement, re-calibration, etc.), and/or quantify any other information.

Additionally or alternatively, S120 can include detecting a set of intoxication events (equivalently referred to herein as drinking events), such as described in any or all of the applications incorporated by reference above.

Additionally or alternatively, S320 can include any other suitable processes.

4.3 Method—Selectively Storing Information

The method 300 can optionally include selectively storing information, which functions to utilize a limited amount of memory onboard the alcohol sensing device for the most useful information to retain. Additionally or alternatively, S330 can function to preserve information for further processing at unknown and/or significantly delayed future times, such as when a user next charges, turns on, uses, and/or syncs (e.g., with a mobile user device) the alcohol sensing device. Additionally or alternatively, S330 can perform any other functions.

S330 is preferably performed in response to the results of S320, wherein data corresponding to events is stored at memory onboard the alcohol sensing device. Additionally or alternatively, S130 can be performed at any other time(s), in response to other triggers, and/or the method 200 can be performed in absence of S330.

In preferred variants, in order to best utilize the limited memory onboard an alcohol sensing device, S330 includes storing (e.g., permanently, temporarily, etc.) data collected during an event and not storing (e.g., not persistently storing, temporarily caching, etc.) data outside of an event. Additionally or alternatively, S330 can include storing a portion of data and/or processed data from an event, which can function to further optimize memory utilization. In some examples, S120 includes detecting an entry and exit of an event, calculating metadata associated with data collected between these times (e.g., average measurement(s), peak and minimum measurement(s), duration of event, etc.), and, in S330, storing the metadata (e.g., along with the associated timestamps as determined with an onboard clock).

In some examples, for instance, an event is detected while the device is operating with only reserve battery, where the device is functionally "dead" to the user and where the user might not charge and turn the device back on for an extended period of time (e.g., months, years, etc.)—S330 can enable this most important event data to be collected and able to be accessed (e.g., when syncing with a mobile user device) after this extended period of time.

Additionally or alternatively, S330 can be otherwise suitably performed and/or include any other processes. For instance, storing information in S330 can include storing test results (e.g., a log of historical test results) at the alcohol sensing device 110 and/or other portions of the systems 100, 200 described above, that have storage capability. Storing information in S330 can alternatively include disabling logging of data logging, such as test results (e.g., a log of historical test results) at the alcohol sensing device 110 and/or other portions of the systems 100, 200 described above, that have storage capability. Storing information in S330 can additionally or alternatively include storing test results (e.g., a log of historical test results) or other data at the alcohol sensing device 110 and/or other portions of the systems 100, 200 described above, that have storage capability, according to various privacy modes. For instance, data stored according to various privacy modes can only allow data to be retrieved by authorized entities (e.g., the user, a monitoring entity associated with the user, etc.) upon verification of the identities of the authorized entities. Verification of the identities of the authorized entities can be performed using biometric sensing elements of the systems 100, 200 described and or other elements described in Applications incorporated by reference.

4.4 Method—Initiating a Set of Actions Based on the Set of Events S140

The method 300 can include initiating a set of actions based on the set of events S340, which can function to: decrease a rate of degradation of an alcohol sensor, prevent the occurrence of a catastrophic event, extend a life of the alcohol sensor, correct measurements collected at the alcohol sensor, and/or can perform any other functions.

S340 is preferably performed in response to and based on the set of health metrics determined in S330, but can additionally or alternatively be performed: in response to a battery (e.g., normal usage portion) of the alcohol sensing device being charged, in response to the alcohol sensing device being synced with a mobile user device, and/or at any other time(s).

The actions that are initiated in S340 can optionally at least partially be determined based on an operation mode associated with the device. This can, for instance, inform any or all of: a type of action that gets initiated (e.g., notification vs. metric correction), a recipient of the action (e.g., user vs. remote monitoring entity), a timing of the action, and/or any other parameters.

S340 preferably includes updating a health metric or meter associated with the alcohol sensor, such as decreasing the metric value by an amount proportional to the amount of damage predicted to have occurred to the alcohol sensor. Additionally or alternatively, an effective age of the sensor can be updated (e.g., increased if exposed to harsh environmental conditions, decreased or increased at a smaller rate when user uses the device, etc.), a number of remaining uses can be decreased, and/or any other metrics can be updated.

In some variants, a user's location (e.g., as determined with a location sensor onboard the device or a mobile user device, based on information input by the user, etc.) or other information (e.g., demographic information, lifestyle information, impact information, etc.) can be used to determine how this metric gets adjusted. For instance, for normal usage of the device by two users, the user who lives in a warm, dry climate can have their sensor health metric decreased more rapidly than the user who lives in a more temperate and/or humid environment.

S340 can additionally or alternatively include adjusting values in the $1^{st}$ subset of data. For instance, as the alcohol sensor health deteriorates (e.g., at a rate determined in S120), the alcohol metrics (e.g., intoxication level, alcohol amount, etc.) determined based on data from the sensor can be adjusted (e.g., scaled, processed with an algorithm, processed with a trained machine learning model, etc.) in accordance with the deterioration. In examples, this is selectively enabled based on the operation mode.

S340 can additionally or alternatively include triggering an intervention for the device, such as: a repair, recalibration, and/or replacement of the alcohol sensor. This can include, for instance automatically shipping a new device or new sensor to the user; automatically transmitting information to the user; automatically sending a calibration system to the user to perform at-home calibration; automatically transmitting a discount on a replacement sensor to the user (e.g., upon detecting that the sensor deterioration is based on usage rather than user carelessness and/or user tampering); and/or any other actions.

In some variants, for instance, an intervention can be automatically triggered once the effective sensor age reaches a predetermined threshold (e.g., 90% of a maximum sensor age defined for the sensor).

S340 can additionally or alternatively include providing information (e.g., notifications, alerts, etc.) to one or more users (e.g., user having alcohol level assessed, remote monitoring entity, etc.), such as through one or more user interfaces (e.g., displays, lights, audio alerts, etc.). The user interfaces can be any or all of: onboard the alcohol sensing device, onboard the mobile user device, and/or at any other components. This information preferably functions to extend a lifetime of the alcohol sensor, providing insights that can help users better maintain their device(s). For instance, the information can alert them to behaviors that degraded the sensor so that they can refrain from such behaviors in the future (e.g., leaving their device in the car); alert them to a degree to which behaviors degraded the device; alert them to a projected date when the alcohol sensor will need to be replaced and/or recalibrated; provide a level of confidence and/or error bars associated with an alcohol measurement; and/or provide any other information.

The information can optionally include, for instance, a visual indicator rendered at a display to the user, where the visual indicator demonstrates how much the alcohol sensor has deteriorated since its first usage. Additionally or alternatively, a rate of deterioration can be determined in S120, which is used to predict a date at which the sensor will need to be replaced, where this date and/or rate is presented to the user. Further additionally or alternatively, an impact of positive behaviors (e.g., moistening the sensor, storing the device in proper conditions, etc.) can be quantified and visualized to the user (e.g., as a change in rate of deterioration, as a reversal of deterioration, etc.).

S340 can additionally or alternatively include adjusting one or more operational parameters (e.g., sampling rate, battery reserve amounts, etc.) based on any or all of the health metrics.

Additionally or alternatively, S340 can include any other suitable processes.

4.5 Method—Variations

As shown in FIG. 2B, variations of the method 300 described above can additionally or alternatively include steps of method 400, where the method 400 includes: performing a first system integrity check with steps for evaluating a set of conditions of an alcohol sensor of an alcohol sensing device S410; performing a second system integrity check with steps for evaluating a set of calibration data generated for the alcohol sensor S420; performing a third system integrity check with steps for evaluating environmental exposure conditions of the alcohol sensing device S430; performing a fourth system integrity check with steps for determining proper function of a pump of the alcohol sensing device S440; performing a fifth system integrity check with steps for evaluating malfunctioning of a processing subsystem and/or the alcohol sensor of the alcohol sensing device S450; and performing a sixth system integrity check with steps for evaluating a deviation between an actual alcohol sensor signal morphology and an expected alcohol sensor signal morphology (e.g., under ambient conditions) of the alcohol sensing device S460.

In some embodiments, the method 400 can further include one or more steps including: receiving a temperature dataset from the temperature sensor S470; comparing a temperature metric to a threshold condition upon processing the temperature dataset S480; determining a time duration from a time point of testing of a previous breath sample received at the sampling subsystem S490; and transmitting instructions for prompting the user to provide a breath sample according to a testing protocol, wherein the testing protocol is modified based upon the temperature metric and the time duration S495.

The methods 300, 400 can be performed using embodiments, variations, and examples of the systems 100, 200 described above. The methods 300, 400 can be performed using embodiments, variations, and examples of system components described in Applications incorporated by reference.

In relation to Step S410, performing the first system integrity check can include verifying electrical coupling of the alcohol sensor (e.g., to other electronics components of the systems described above), such that the set of conditions includes an electrical coupling condition. In an example, verifying electrical coupling of the alcohol sensor involves steps for testing capacitance (e.g., exercising a dual-layer capacitance, evaluating dual-layer capacitance) of the alcohol sensor (in embodiments where the alcohol sensor is a fuel cell sensor), in order to confirm that the alcohol sensor is still suitably coupled to other electronics components of the systems described. For other sensor types, verifying electrical coupling of the alcohol sensor can include applying test electrical signals (e.g., in relation to applied currents, applied voltages, etc.), and measuring an electrical signal (e.g., current signal, voltage signal, resistance, other signal) associated with the alcohol sensor.

In relation to Step S410, performing the first system integrity check can involve determining an age of the alcohol sensor, such that the set of conditions includes a sensor age condition. Determining an age of the alcohol sensor functions to determine if the age of the alcohol sensor is above a threshold age, such that results generated would be invalid or inaccurate. Determining the age of the alcohol sensor can include tracking or otherwise determining one or more of: a number of uses of the alcohol sensor (e.g., in relation to number of testing events); an age of the alcohol sensor determined from a manufacture time point to a current time point; an age of the alcohol sensor determined from a date of first use to a current time point; an estimated age of the alcohol sensor determined from an initial time point (e.g., time of first use, time of manufacture, etc.), historical data capturing ambient conditions of use of the alcohol sensor, number of uses of the alcohol sensor in relation to testing events, and/or other factors; and determining age in another suitable manner.

In relation to Step S420, performing the second system integrity check with steps for evaluating a set of calibration data generated for the alcohol sensor functions to determine if calibration data associated with calibration of the alcohol sensor is corrupted or otherwise invalid, if the systems described are due for calibration, and/or if the system(s) is/are overdue for re-calibration. Evaluating the set of calibration data can involve performing a calibration operation with a zero alcohol sample (e.g., a breath sample provided by the user, where the user has not consumed alcohol or any substance that would otherwise produce a non-zero alcohol content value during testing). As such, performing the calibration operation can include processing a zero alcohol sample with the alcohol sensor. The calibration operation can be performed using systems and/or according to method steps described in U.S. application Ser. No. 15/492,216 filed on 20 Apr. 2017, which is herein incorporated in its entirety by this reference.

In relation to the second system integrity check of Step S420, determining if the system is due for calibration or overdue for re-calibration can include tracking or otherwise determining one or more of: a time point of a prior calibration event; a number of calibration events performed over the lifetime of use of the system; a change in ambient conditions associated with the system; a change in device status associated with the system; a determination of a period of disuses of the system; a determination of a period of disuse of the system followed by a period of use of the system; a number of uses of the alcohol sensor (e.g., in relation to number of testing events); an age of the alcohol sensor determined from a manufacture time point to a current time point; an age of the alcohol sensor determined from a date of first use to a current time point; an estimated age of the alcohol sensor determined from an initial time point (e.g., time of first use, time of manufacture, etc.), historical data capturing ambient conditions of use of the alcohol sensor, number of uses of the alcohol sensor in relation to testing events, and/or other factors; and other suitable parameters associated with calibration of the system.

In relation to Step S430, performing the third system integrity check with steps for evaluating environmental exposure conditions of the system functions to determine if the alcohol sensing device has been exposed to extreme conditions (e.g., extreme temperature conditions, extreme humidity conditions, extreme pressure conditions, extreme mechanical forces, etc.) and/or any conditions outside of specified storage conditions. Performing the third system integrity check can include interrogating one or more sensors of the set of supplementary sensors (e.g., temperature sensors, pressure sensors, humidity sensors, accelerometers, light sensors, etc.) described, and comparing conditions represented in data resulting from interrogation, to threshold conditions indicative of exposure to extreme conditions. In variations, performing the third system integrity check comprises processing a temperature dataset from the temperature sensor and determining if a temperature to which the alcohol sensing device was subjected was greater than a threshold temperature. In examples, a threshold temperature condition can be a temperature greater than 90F, greater than 95F, greater than 100F, greater than 110F, greater than 120F, or greater. In examples, a threshold pressure condition can be a temperature greater than 15 PSI, 18 PSI, 20 PSI, 22 PSI, 24 PSI, 26 PSI, 28 PSI, 30 PSI, or greater. In examples, a threshold humidity condition can be a humidity greater than 90% relative humidity, 95% relative humidity, or greater.

In relation to Step S440, performing the fourth system integrity check with steps for determining proper function of the pump functions to determine if the pump is electrically connected and functioning properly. In an example, verifying electrical coupling of the pump involves steps for testing voltage across the pump (e.g., measuring a voltage across the pump), in order to confirm that the pump is still suitably coupled to other electronics components of the system. For other sensor types, verifying electrical coupling of the pump 240 can include applying test electrical signals (e.g., in relation to applied currents, applied voltages, etc.), and measuring an electrical signal (e.g., current signal, voltage signal, resistance, other signal) associated with the pump. Determining proper function of the pump can also involve performing a test run of the pump (e.g., with verification that the pump is pressurizing and/or depressurizing as expected).

In relation to Step S450, performing the fifth system integrity check with steps for evaluating malfunctioning of the processing subsystem and/or the alcohol sensor functions to determine if previous sample tests have resulted in critical errors that indicate that the algorithm by which the alcohol sensing device operates is malfunctioning, and/or any sensors of the system are malfunctioning. Performing the fifth system integrity check can include evaluating a log of prior sample test data to determine if any errors have been detected and not resolved. Performing the fifth system integrity check can then include resolving any detected errors or malfunctions, and/or notifying the user or another entity that the alcohol sensing device is not operating properly and should be replaced.

In relation to Step S460, performing the sixth system integrity check includes steps for evaluating a deviation between an actual alcohol sensor signal morphology and an expected alcohol sensor signal morphology (e.g., under ambient conditions). Performing the sixth system integrity check can involve a cloud-based analysis of raw data from previous test results involving the alcohol sensing device 110. The cloud-based analysis can be performed upon pairing the alcohol sensing device 110 with a mobile computing device (e.g., a mobile computing device associated with the user), which has a link to a cloud-based computing processor for analyzing the alcohol sensor signal. Alternatively, the cloud-based analysis can be performed with a direct link between the alcohol sensing device 110 and the cloud-based computing processor. Still alternatively, the sixth system integrity check can be performed on-board the alcohol sensing device, in embodiments wherein the alcohol sensing device includes edge-deployed sensors and processors (e.g., neural processing units) capable of performing the analysis. Performing the sixth system integrity check can include determining if the alcohol sensor signals fit an expected shape. In a specific example, performing the sixth system integrity check can include curve fitting alcohol sensor signals against an ideal anatomy of the signal (e.g., under ambient conditions, under standard temperature, under standard pressure, under another suitable standard condition), where the ideal anatomy of the signal can take the form of equation [1] above, and repeated below.

$$f(x)=a*(e^{\char`\^}(-b*x)-e^{\char`\^}(-(b/c)*x)) \qquad [1]$$

In the specific example, performing the sixth system integrity check according to Step S460 can then include determining significant deviations of the alcohol sensor signal from the expected signal shape (e.g., based upon determination of coefficients of equation [1] in comparison to threshold values for such coefficients]. Performing the sixth system integrity check can then include resolving any issues associated with unexpected signal shapes (e.g., re-calibrating the alcohol sensor, etc.), and/or notifying the user or another entity that the alcohol sensing device 110 is not operating properly and should be replaced. The variations of the sixth system integrity check can additionally or alternatively be performed using systems and/or according to method steps described in U.S. application Ser. No. 15/492,216 filed on 20 Apr. 2017, which is herein incorporated in its entirety by this reference.

Figure 9:
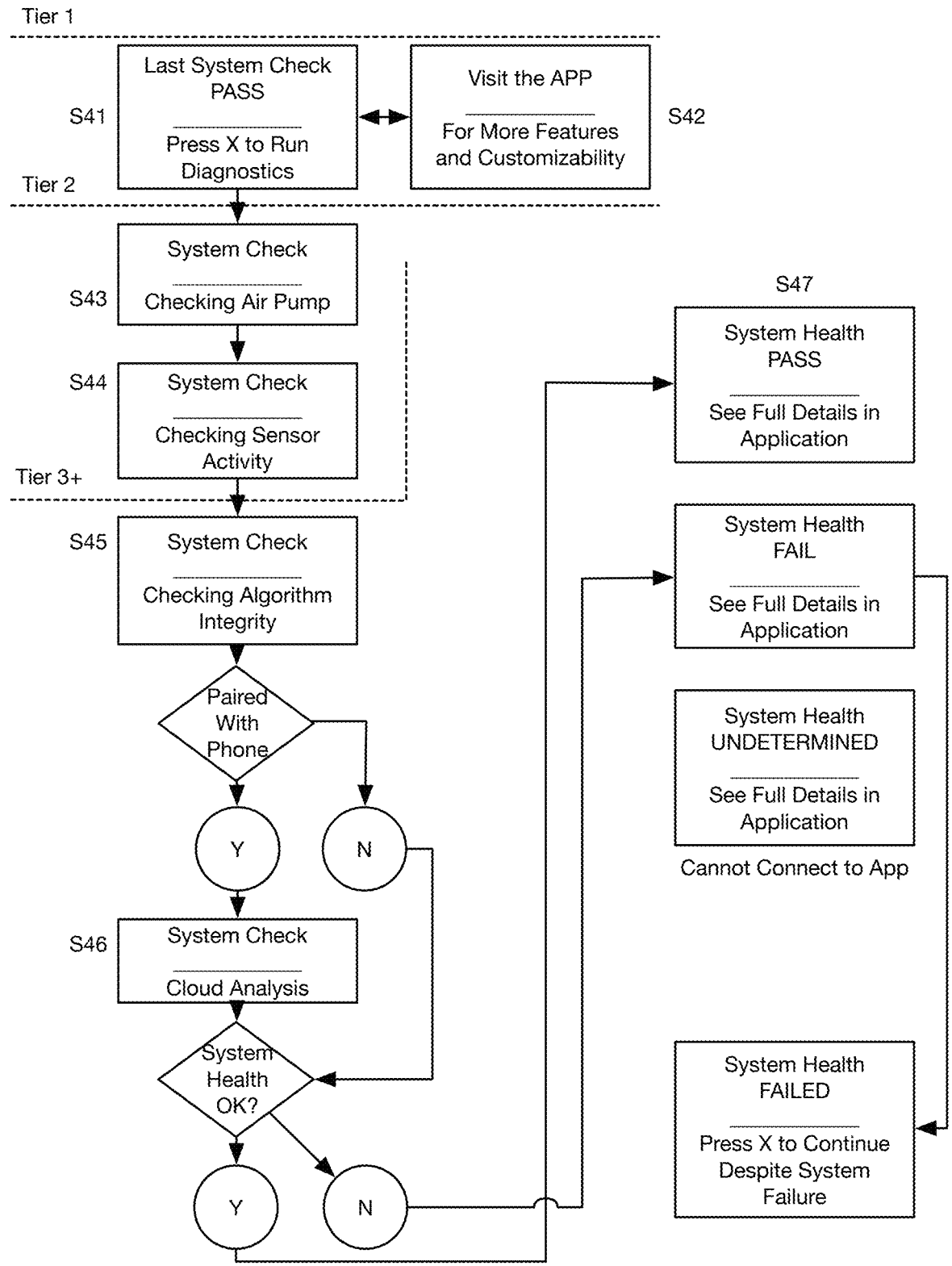
FIG. 9 depicts an example of a workflow for running a set of system integrity checks, for an alcohol sensing device.

An example of a system integrity check workflow is depicted in FIG. 9, which shows a set of tiers of system integrity checks and related operations. The example of the system integrity check workflow includes: evaluating a passing state of a prior check of the system S41 (e.g., as a Tier 1 step); a prompt to visit a mobile device application supporting the alcohol sensing device for more features and customizability S42 (e.g., as a Tier 1 step); a step for checking the pump of the alcohol sensing device upon passing conditions of the prior check S43 (e.g., as a Tier 2 step), where S43 involves running the pump, light emitting devices, vibration devices, and other system components through their ranges of operational states (e.g., for 10 seconds); a step for checking sensor activity of the set of sensors of the alcohol sensing device S44 (e.g., as a Tier 2 step), where the sensor tests must fail if calibration data indicates that the calibration is overdue or faulty; a step for determining algorithm integrity S45 (e.g., as a Tier 3 step, where algorithm integrity can be performed according to embodiments, variations, and examples of the fifth system integrity check described); a step for performing a cloud-based analysis S46 (e.g., as a Tier 3 step, where algorithm integrity can be performed according to embodiments, variations, and examples of the sixth system integrity check described) where, if a device is paired, the device Broadcasts a beacon (e.g., Bluetooth™ beacon signal) and waits (e.g., ~10 seconds) for a connection from a mobile computing device. Then, if a connection occurs, a PASS or FAIL determination is provided from the cloud-based analysis; and a step for indicating passing, failing, or indeterminate results of the set of system integrity checks S47. Passing results can have a time-based expiration date, where determination that the alcohol sensing device is past the time-based expiration date can be used to trigger a subsequent run of the set of system integrity checks. In the example, if the set of system integrity checks results in a failing status, every time the user attempts to access the alcohol sensing device to provide a sample, they are prompted to acknowledge and confirm via an alert/error notification (e.g., with emitted light colors, with messages indicating that they would be continuing to provide samples despite system failure or inaccuracy).

The method 400 can further include Step S465, which recites: prompting the user to provide a breath sample to the alcohol sensing device upon satisfaction of one or more of: the first system integrity check, the second system integrity check, the third system integrity check, the fourth system integrity check., the fifth system integrity check, the sixth system integrity check, and/or other system integrity checks.

Prompting the user to provide a breath sample in Step S465 can include prompting the user to provide a timed breath sample (e.g., a breath sample provided according to a duration of time requirement). Prompting for the timed breath sample can include guiding the user (e.g., through a user interface described) to provide a breath sample for a duration of up to 5 seconds, for a duration of up to 7 seconds, for a duration of up to 10 seconds, or for another suitable duration.

Prompting the user to provide a breath sample in Step S465 can additionally or alternatively include prompting the user to provide a volumetric breath sample (e.g., a breath sample provided according to a sample volume requirement). The sampling subsystem can meter a specified sample volume for processing at the alcohol sensor. Additionally or alternatively processing subsystem described can track the amount of sample provided for processing. The volume of sample can be up to 1500 mL, up to 2000 mL, up to 2500 mL, up to 3000 mL, up to 3500 mL, up to 4000 mL, up to 4500 mL, up to 5000 mL, up to 5500 mL, or of another suitable volume.

Prompting the user to provide a breath sample in Step S465 can additionally or alternatively include prompting the user to provide a deep lung breath sample. In processing a deep lung breath sample, a pump of the system(s) described above can drive flow of a portion of the sample, associated with breath from a deep lung volume of air, across the alcohol sensor. In variations, for a breath sample that is provided for a duration of time, the pump can be configured to transition to a driving mode for only a portion of the duration of time, such that only a portion of the breath sample is driven across the alcohol sensor. In specific examples, an average breath sample volume provided into the flow tube during a five second sample is about 5,000 mL. The first 3,500 mL can be disregarded because it comes from the mouth and esophagus, which often have a higher alcohol content than the actual BAC value of the user. As such, in specific examples of Step S465 for deep lung samples, the pump can be configured to transition to a driving mode to drive only a portion (e.g., final portion, final 1500 mL portion, final 1000 mL portion, final 500 mL portion, final 250 mL portion, etc.) of the breath sample across the alcohol sensor. This operation mode ensures that the breath sample provided to the alcohol sensor arrives from one direction, which is important for accuracy, and also only allows air from the deepest part of the lungs to be tested for accurate measurement of BAC. As such, in variations, the pump is configured to drive a portion of the sample (and omit driving a remainder of the sample) across the alcohol sensor, wherein the portion of the sample is associated with a deep lung volume of air from the user.

In relation to Step S465, prompting the user to provide a breath sample can include dynamically modifying prompting of a type of breath sample (e.g., a timed breath sample, a volumetric breath sample, a deep lung breath sample, a transdermal sample, etc.) to be received from the user, depending upon a condition of the user. For instance, if the user is running out of air (e.g., when prompted to provide a timed breath sample, when prompted to provide a volumetric breath sample, etc.), modifying prompting can include prompting to provide a different type of breath sample than the type of breath sample originally requested. In another example, the processing subsystem can include architecture for detecting when the lungs of the user are exhausted (e.g., based upon body size of the user, medical history of the user, demographics of the user, etc.), and prompt the user to provide a type of breath sample based upon the detection of exhaustion. In another example, Step S465 can include prompting the user to provide a type of breath sample, where the prompt is customized based upon based upon body size (e.g., weight, BMI, height, lung capacity, etc.) of the user, medical history of the user, demographics of the user (e.g., gender, age, etc.), physical activity of the user, and/or other factors. Calibration (e.g., of alcohol sensor signals) within sampling modes can be further customized based upon body size (e.g., weight, BMI, height, lung capacity, etc.) of the user, medical history of the user (e.g., if the user has been affected by SARS-COV-2, if the user has been affected by another coronavirus, if the user has been affected by an influenza virus, if the user has been affected by respiratory syncytial virus, if the user has been affected by another virus or bacteria, if the user has Chronic Obstructive Pulmonary Disease, if the user has a respiratory health condition, etc.), demographics of the user (e.g., gender, age, etc.), physical activity of the user, and/or other factors.

Providing the breath sample can additionally or alternatively be performed according to embodiments, variations, and examples of sample provision and reception steps described in Applications incorporated by reference.

In relation to the systems described, the alcohol sensing device can be configured to be always on, as long as the power source has sufficient power to power the system. A clock of the system enables the system to thus retain a sense of time and to determine when a prior sample was processed by the alcohol sensor, in comparison to other alcohol sensing devices that do not retain a sense of time between sample testing events. Such systems that do not retain a sense of time thus must automatically require a standard clearing time (given that there is no ability to determine when a prior sample was received), before receiving another sample in order to ensure testing accuracy, where the standard clearing time ensures clearing of the alcohol sensor such that it can be used to accurately test a new sample. The standard clearing time can be a duration of up to 30 seconds, up to 1 minute, up to 1.5 minutes, up to 2 minutes, up to 2.5 minutes, up to 3 minutes, up to 3.5 minutes, up to 4 minutes, up to 4.5 minutes, up to 5 minutes, up to 5.5 minutes, up to 6 minutes, up to 6.5 minutes, up to 7 minutes, up to 7.5 minutes, up to 8 minutes, up to 8.5 minutes, up to 9 minutes, or greater than 9 minutes.

As such, in relation to Step S470, receiving a temperature dataset from the temperature sensor can include receiving signals indicate of device temperatures, ambient environmental temperatures, and/or other temperatures associated with the system(s) for sample reception and processing.

In relation to Step S480, comparing a temperature metric to a threshold condition upon processing the temperature dataset can include determining if the temperature is above or below a suitable temperature for processing of the breath sample by the alcohol sensor. In variations, an upper threshold temperature can be a threshold temperature condition greater than 90F, greater than 95F, greater than 100F, greater than 110F, greater than 120F, or greater. In variations, a lower threshold temperature can be a threshold temperature condition less than 50F, less than 45F, less than 40F, less than 35F, less than 30F, or less. Upon determination that the temperature metric is above the high threshold temperature, the processing subsystem can perform an action, wherein, in examples, the action can include one or more of: activating a cooling element (e.g., fan) of the system to cool the alcohol sensing device and/or alcohol sensor to below the threshold temperature; guiding the user to bring the alcohol sensing device to a cooler environment, prohibiting the user from providing a sample while the temperature is above the threshold temperature, storing a received sample and metering the sample by way of the pump, when the temperature falls below the threshold temperature, and performing other suitable actions. Upon determination that the temperature metric is below the low threshold temperature, the processing subsystem can perform an action, wherein, in examples, the action can include one or more of: activating a heating element (e.g., heater) of the system to heat the alcohol sensing device and/or alcohol sensor to above the threshold temperature; guiding the user to bring the alcohol sensing device to a warmer environment, prohibiting the user from providing a sample while the temperature is below the threshold temperature, storing a received sample and metering the sample by way of the pump, when the temperature rises above the threshold temperature, and performing other suitable actions.

In relation to Step S480, determining a time duration from a time point of testing of a previous breath sample received at the sampling subsystem can include determining when the prior breath sample was received, by way of the clock of the system, determining a current time point, and determining a difference between the current time point and the time point of testing of the previous breath sample.

In relation to Step S490, transmitting instructions for prompting the user to provide a breath sample according to a testing protocol, wherein the testing protocol is modified based upon the temperature metric and the time duration, can be performed using the user interface(s) of the systems described. Given that the system retains a sense of time, modification of the testing protocol can include prompting the use to provide a breath sample without requiring the user to unnecessarily wait according to a standard clearing time requirement, upon determination that a duration of time has passed after the system 200 has processed a prior sample, and the duration of time satisfies the standard clearing time requirement. In a specific example, the processing system 290 can determine that a prior sample was received and processed 6 minutes before a current time point, which satisfies the standard clearing time requirement. The user can thus be prompted to provide a sample for processing without unnecessarily waiting an additional duration of time (e.g., a minimum wait time for sensor clearing has been exceeded). Such steps of the method 400 can thus streamline and improve rapidness of user testing, whereby, in many situations, the user can, whenever the user desires or is prompted, provide a sample and receive test results within an unprecedented duration of time. The duration of time can be less than 30 seconds, less than 25 seconds, less than 20 seconds, less than 19 seconds, less than 18 seconds, less than 17 seconds, less than 16 seconds, less than 15 seconds, less than 14 seconds, less than 13 seconds, less than 12 seconds, less than 11 seconds, less than 10 seconds, or less.

Related to the clock, the method 400 can include indicating, on a user interface of the alcohol sensing device, a time point (e.g., actual time point, anticipated time point, estimated time point) at which the user will return to a zero alcohol content state, or a state where the alcohol content of the user will be less than a threshold value (e.g., less than 0.8 BAC or equivalent). The clock thus enables precise time-based estimates of alcohol content of the user, on-device, where associated notifications can also be provided to the user using the user interface components of the alcohol sensing device. Aspects of alcohol content state estimation can be implemented, and embodiments, variations, and examples are described in U.S. application Ser. No. 14/169,029 filed on 30-Jan.-2014 and now issued as U.S. Pat. No. 8,878,669 on 4 Nov. 2014, which is herein incorporated in its entirety by this reference.

In some variations, the method 400 can further include Step S497, which recites: triggering an action in response to evaluation of at least one of the alcohol sensor and the alcohol sensing device according to a set of system integrity checks (e.g., the first system integrity check, the second system integrity check, the third system integrity check, the fourth system integrity check, the fifth system integrity check, the sixth system integrity check, etc.).

The triggered action can include providing a notification to the user and/or an entity (e.g., platform manager) associated with evaluating states of the alcohol sensing device. The notification can be automatically transmitted to the user and/or entity through embodiments, variations, and examples of the user interface(s) described above. The notification can be automatically generated from use of generative artificial intelligence (AI) architecture (e.g., involving large language models) and/or other models. Additionally or alternatively, the notification can be generated without use of generative AI architecture. In examples, notifications and/or other information transmitted to the user(s)/entity (ies) through the user interface(s) described can be modified to have a specific style (e.g., serious style, casual style, etc.). In one example, the notifications and/or other information can mimic a style of an enforcement personnel. The notifications and/or other information transmitted to the user(s)/entity (ies) through the user interface(s) described can be educational in nature (e.g., providing information regarding how alcohol sensors work, providing information regarding calibration states of the alcohol sensor, providing information regarding proper use and handling of the alcohol sensing device, etc.). In example, a notification provided to the user can include information informing the user that the alcohol sensing device is being stored in a manner that is outside of the proper storage conditions specified (e.g., inside of a hot vehicle when ambient conditions are greater than 100F, etc.). In another example, a notification provided to the user can include prompting the user to move the alcohol sensing device to conditions that are within the proper storage conditions specified (e.g., to move the alcohol sensing device from a hot vehicle environment to being stored in a carrier). In another example, a notification provided to the user can include information informing the user that the pump is no longer connected, and that a sample should not be provided to the alcohol sensing device.

The notifications and/or other information transmitted to the user(s)/entity (ies) through the user interface(s) described can be customized to the user. The notifications and/or other information transmitted to the user(s)/entity (ies) through a user interface on-board the alcohol sensing device and/or incorporated into an application of a mobile computing device associated with the user (e.g., an application where the user has a user account). Notifications and/or other information can be indicated through color or other observable signals broadcast using elements of the alcohol sensing device. In one example, a notification that the alcohol sensing device is unsuitable for use (e.g., fouled, having a faulty alcohol sensor, having an uncalibrated alcohol sensor, etc.) can be provided using light emitting elements of the alcohol sensing device (e.g., lights of the alcohol sensing device can transition emitted colors from green to yellow or red, if the alcohol sensor is in a less suitable condition for use).

In relation to configurations where the alcohol sensing device can be configured to be always on or hibernating (e.g., as long as the power source has sufficient power to power the system), triggered actions can include performing operations during on states and hibernating/asleep states of the alcohol sensing device. In variations, actions can include performing a tangential set of checks to the set of system integrity checks, while the alcohol sensing device is in a hibernating/asleep state (e.g., where the device appears to be off, but has some active operation modes). In the hibernating mode of operation, the alcohol sensing device can thus evaluate signals according to the tangential set of checks (e.g., of temperature, of other metrics) of the alcohol sensing device at a set of time points between processing of samples provided by the user.

In examples, the tangential set of checks can include one or more of: processing a set of signals from the set of supplementary sensors (e.g., temperature sensors, pressure sensors, humidity sensors, etc.) in order to assess conditions of an ambient environment surrounding the alcohol sensing device (e.g., akin to the third system integrity check S430). The tangential set of checks can include detecting high mechanical stress events (e.g., dropping of the alcohol sensing device, an impact to the alcohol sensing device, crushing of the alcohol sensing device, throwing of the alcohol sensing device, etc.), by way of an accelerometer or other sensor of the alcohol sensing device. The tangential set of checks can include detecting tampering with the alcohol sensing device, where detecting tampering can include detecting if a housing of the alcohol sensing device has been opened (e.g., upon detection of a disruption involving electrical signals associated with electronics of the alcohol sensing device, upon detection of a mechanical breaking force applied to the housing of the alcohol sensing device, etc.). Detecting tampering can be performed according to embodiments, variations, and examples of methods described in U.S. application Ser. No. 17/033,501 filed on 25 Sep. 2020 and now issued as U.S. Pat. No. 11,324,449 on 10 May 2022 and U.S. patent Ser. No. 18/109,720 filed on 14 Feb. 2023, which are each incorporated in its entirety herein by this reference.

Processing signals associated with the tangential set of checks can be performed using an embodiment, variation, or example of processing subsystems described above.

The tangential set of checks can be performed at a regular frequency, intermittently, or in response to a detected state (e.g., when the user is near a home location as detected using GPS of the mobile device, when the user is in proximity to a location where alcohol could be served as detected using GPS of the mobile computing device, when the user is near a vehicle as detected using vehicle pairing systems, etc.) during the hibernating/asleep state. In examples, the regular frequency can be a frequency of: every minute, every two minutes, every three minutes, every four minutes, every 5 minutes, every 10 minutes, every 15 minutes, every 30 minutes, every hour, every 2 hours, every 3 hours, every 5 hours, every 10 hours, or at another suitable frequency.

The triggered action can additionally or alternatively include one or more of: a repair, recalibration, and replacement of the alcohol sensor. In variations, replacement of alcohol sensor can include, for instance, automatically shipping a new alcohol sensing device or new sensor to the user. In variations, recalibration can include automatically sending a calibration system to the user to perform at-home calibration. In variations, triggering replacement can include automatically transmitting a discount on a replacement sensor to the user (e.g., upon detecting that the sensor deterioration is based on usage rather than user carelessness and/or user tampering), in relation to the set of system integrity checks.

4.6 Method—Additional Processes

The methods 300, 400 can additionally or alternatively include any other processes, such as, but not limited to: training one or more algorithms and/or models, updating and/or retraining one or more models and/or algorithms, and/or any other processes. In some variants, for instance, a machine learning model can be trained (e.g., based on data from devices sent back for replacement and/or recalibration, based on simulated environmental conditions, etc.) and iteratively updated (e.g., retrained, tuned, etc.) as new information is received.

Additionally or alternatively, the method 200 can include any other processes.

Although omitted for conciseness, the preferred embodiments include every combination and permutation of the various system components and the various method processes, wherein the method processes can be performed in any suitable order, sequentially or concurrently.

Embodiments of the system and/or method can include every combination and permutation of the various system components and the various method processes, wherein one or more instances of the method and/or processes described herein can be performed asynchronously (e.g., sequentially), contemporaneously (e.g., concurrently, in parallel, etc.), or in any other suitable order by and/or using one or more instances of the systems, elements, and/or entities described herein. Components and/or processes of the following system and/or method can be used with, in addition to, in lieu of, or otherwise integrated with all or a portion of the systems and/or methods disclosed in the applications mentioned above, each of which are incorporated in their entirety by this reference.

Additional or alternative embodiments implement the above methods and/or processing modules in non-transitory computer-readable media, storing computer-readable instructions. The instructions can be executed by computer-executable components integrated with the computer-readable medium and/or processing system. The computer-readable medium may include any suitable computer readable media such as RAMs, ROMs, flash memory, EEPROMs, optical devices (CD or DVD), hard drives, floppy drives, non-transitory computer readable media, or any suitable device. The computer-executable component can include a computing system and/or processing system (e.g., including one or more collocated or distributed, remote or local processors) connected to the non-transitory computer-readable medium, such as CPUs, GPUs, TPUS, microprocessors, or ASICs, but the instructions can alternatively or additionally be executed by any suitable dedicated hardware device.

As a person skilled in the art will recognize from the previous detailed description and from the figures and claims, modifications and changes can be made to the preferred embodiments of the invention without departing from the scope of this invention defined in the following claims.

We claim:

1. A method comprising: for an alcohol sensing device comprising a flow tube, an alcohol sensor in communication with the flow tube, a pump configured to deliver breath samples from the user through the flow tube and to the alcohol sensor, the method comprising:
    performing a first system integrity check with steps for evaluating a set of conditions of the alcohol sensor;
    performing a second system integrity check with steps for evaluating a set of calibration data generated for the alcohol sensor;
    performing a third system integrity check with steps for evaluating environmental exposure conditions of the alcohol sensing device;
    performing a fourth system integrity check with steps for determining proper function of the pump, wherein the pump comprises a solenoid pump, and wherein performing the fourth system integrity check comprises verifying electrical coupling of the pump upon measuring a voltage across the pump;
    performing a fifth system integrity check with steps for evaluating malfunctioning of the alcohol sensor; and
    performing a sixth system integrity check with steps for evaluating a deviation between an actual alcohol sensor signal morphology and an expected alcohol sensor signal morphology for the alcohol sensor.

2. The method of claim 1, wherein the alcohol sensor comprises a fuel cell sensor, and wherein the set of conditions comprises an electrical coupling condition.

3. The method of claim 1, wherein the set of conditions comprises a sensor age condition, and wherein performing the first system integrity check comprises determining an age of the alcohol sensor based upon a number of uses of the alcohol sensor.

4. The method of claim 1, wherein performing the second system integrity check comprises performing a calibration operation upon processing a zero alcohol sample with the alcohol sensor.

5. The method of claim 1, wherein the alcohol sensing device comprises a temperature sensor, and wherein performing the third system integrity check comprises processing a temperature dataset from the temperature sensor and determining if a temperature to which the alcohol sensing device was subjected was greater than a threshold temperature.

6. The method of claim 1, wherein performing the sixth system integrity check comprises evaluating a deviation between an actual alcohol sensor signal morphology and an expected alcohol sensor signal morphology derived from signals from the alcohol sensor, wherein evaluating the deviation comprises comparing coefficients of a curve fitted to the actual alcohol sensor signal morphology to a set of threshold coefficient values.

7. The method of claim 1, further comprising prompting the user to provide a breath sample to the alcohol sensing device upon satisfaction of the first system integrity check, the second system integrity check, the third system integrity check, the fourth system integrity check, the fifth system integrity check, and the sixth system integrity check.

8. The method of claim 1, wherein the alcohol sensing device further comprises a temperature sensor, the method further comprising:
    receiving a temperature dataset from the temperature sensor;
    comparing a temperature metric to a temperature threshold condition upon processing the temperature dataset,
    transmitting instructions for prompting the user to provide a breath sample to the alcohol sensing device according to a testing protocol, wherein the testing protocol is modified based upon the temperature metric.

9. The method of claim 8, wherein upon determining that the temperature metric is above the temperature threshold condition, the method comprises notifying the user to relocate the alcohol sensing device to a location that satisfies the temperature threshold condition.

10. The method of claim 8, wherein the alcohol sensing device comprises a hibernating mode of operation wherein the alcohol sensing device evaluates temperature of the alcohol sensing device at a set of time points between processing of samples provided by the user.

11. The method of claim 1, wherein the alcohol sensing device further comprises a clock, the method further comprising:
    determining a time duration from a time point of testing of a previous breath sample received at the alcohol sensing device; and
    transmitting instructions for prompting the user to provide a breath sample to the alcohol sensing device according to a testing protocol, wherein the testing protocol is modified based upon the time duration.

12. The method of claim 11, wherein modification of the testing protocol comprises prompting the user to provide a breath sample to the alcohol sensing device without requiring the user to unnecessarily wait according to a standard clearing time for the alcohol sensor.

13. The method of claim 12, wherein receiving the breath sample and receiving test results of the breath sample from the alcohol sensing device is performed in less than 20 seconds.

14. A system for monitoring intoxication of a user, the system comprising:
    a sampling subsystem comprising a flow tube, an alcohol sensor in communication with the flow tube, and a solenoid pump configured to deliver breath samples from the user through the flow tube and to the alcohol sensor;
    a housing surrounding the sampling subsystem;

a mouthpiece coupled to the flow tube of the sampling subsystem;
a temperature sensor retained within the housing;
a first user interface; and
a processing subsystem at least partially disposed within the housing and comprising a clock, wherein the processing subsystem:
receives a temperature dataset from the temperature sensor,
compares a temperature metric to a threshold condition upon processing the temperature dataset,
determines a time duration from a time point of testing of a previous breath sample received at the sampling subsystem, and
transmits instructions for prompting the user to provide a breath sample according to a testing protocol, wherein the testing protocol is modified based upon the temperature metric and the time duration; and
wherein the processing subsystem further comprises instructions stored in non-transitory media for performing a set of system integrity checks prior to reception of a breath sample from the user, wherein performing a system integrity check of the set of system integrity checks comprises verifying electrical coupling of the pump upon measuring a voltage across the pump.

15. The system of claim 14, wherein the set of system integrity checks comprises: a first system integrity check with steps for evaluating a set of conditions of the alcohol sensor; a second system integrity check with steps for evaluating a set of calibration data generated for the alcohol sensor; a third system integrity check with steps for evaluating environmental exposure conditions of the alcohol sensor; a fifth system integrity check with steps for evaluating malfunctioning of the alcohol sensor; and a sixth system integrity check with steps for evaluating a deviation between an actual alcohol sensor signal morphology and an expected alcohol sensor signal morphology of signals received from the alcohol sensor.

16. The system of claim 15, wherein the alcohol sensor comprises a fuel cell sensor, wherein the set of conditions comprises an electrical coupling condition and a sensor age condition, and wherein performing the first system integrity check comprises determining an age of the alcohol sensor based upon a number of uses of the alcohol sensor for satisfaction of the sensor age condition.

17. The system of claim 15, the third system integrity check involves processing a temperature dataset from the temperature sensor and determining if a temperature to which the alcohol sensing device was subjected was greater than a threshold temperature.

18. The method of claim 14, wherein the mouthpiece comprises a near-field communication (NFC) element.

* * * * *

UNITED STATES PATENT AND TRADEMARK OFFICE
CERTIFICATE OF CORRECTION

Page 1 of 1

PATENT NO. : 12,343,133 B1
APPLICATION NO. : 18/922156
DATED : July 1, 2025
INVENTOR(S) : Keith Nothacker et al.

It is certified that error appears in the above-identified patent and that said Letters Patent is hereby corrected as shown below:

On the Title Page

Column 1, Item (72) Inventors, Line 4, Delete "Francsico," and insert --Francisco,-- therefor In the Claims Column 35, Line 29, In Claim 1, after "method", delete "comprising:"

Signed and Sealed this
Twelfth Day of August, 2025

Coke Morgan Stewart
*Acting Director of the United States Patent and Trademark Office*